(12) United States Patent
Foscante

(10) Patent No.: US 9,078,445 B2
(45) Date of Patent: Jul. 14, 2015

(54) ANTIMICROBIAL CHEMICAL COMPOSITIONS

(75) Inventor: Raymond E. Foscante, Yorba Linda, CA (US)

(73) Assignee: BUNGE AMORPHIC SOLUTIONS LLC, White Plains, NY (US)

( * ) Notice: Subject to any disclaimer, the term of this patent is extended or adjusted under 35 U.S.C. 154(b) by 59 days.

(21) Appl. No.: 13/448,253

(22) Filed: Apr. 16, 2012

(65) Prior Publication Data

US 2013/0274372 A1    Oct. 17, 2013

(51) Int. Cl.
| | | |
|---|---|---|
| A01N 59/00 | (2006.01) | |
| A01N 59/26 | (2006.01) | |
| A01N 25/10 | (2006.01) | |
| C01B 25/45 | (2006.01) | |
| C09D 5/14 | (2006.01) | |
| A01N 59/06 | (2006.01) | |

(52) U.S. Cl.
CPC . *A01N 59/06* (2013.01); *C09D 5/14* (2013.01)

(58) Field of Classification Search
CPC ... A01N 59/06; A01N 2300/00; A01N 25/10; C09D 5/14
USPC .......... 523/122; 524/403, 413, 414, 415, 432
See application file for complete search history.

(56) References Cited

U.S. PATENT DOCUMENTS

| | | |
|---|---|---|
| 1,654,404 A | 12/1927 | Blumenberg, Jr. |
| 2,222,196 A | 11/1940 | Vilkomerson |
| 2,222,199 A | 11/1940 | Fleck |
| 3,394,987 A | 7/1968 | Lee et al. |
| 3,650,683 A | 3/1972 | Hloch et al. |
| 3,801,704 A | 4/1974 | Kobayashi et al. |
| 3,926,905 A | 12/1975 | Nose et al. |
| 3,943,231 A | 3/1976 | Wasel-Nielen et al. |
| 4,015,050 A | 3/1977 | Birchall et al. |
| 4,054,678 A | 10/1977 | Benjamin et al. |
| 4,076,221 A | 2/1978 | Groger |
| 4,078,028 A | 3/1978 | Kishi |
| 4,098,749 A | 7/1978 | Hoshino et al. |
| 4,111,884 A | 9/1978 | Takase et al. |
| 4,122,231 A | 10/1978 | Kishi |
| 4,127,157 A | 11/1978 | Gardikes et al. |
| 4,138,261 A | 2/1979 | Adrian et al. |
| 4,147,758 A | 4/1979 | Adrian et al. |
| 4,169,802 A | 10/1979 | Basile et al. |
| 4,171,984 A | 10/1979 | Hosaka et al. |
| 4,216,190 A | 8/1980 | Neely, Jr. |
| 4,227,932 A | 10/1980 | Leah et al. |
| 4,260,591 A | 4/1981 | Benjamin et al. |
| 4,319,926 A | 3/1982 | Nowakowski et al. |
| 4,321,244 A | 3/1982 | Magnier et al. |
| 4,328,033 A | 5/1982 | Boberski et al. |
| 4,329,327 A | 5/1982 | Neely, Jr. et al. |
| 4,333,914 A | 6/1982 | Neely, Jr. et al. |
| 4,364,854 A | 12/1982 | McDaniel et al. |
| 4,364,855 A | 12/1982 | McDaniel et al. |
| 4,375,496 A | 3/1983 | Nowakowski et al. |
| 4,383,866 A | 5/1983 | Nowakowski et al. |
| 4,395,387 A | 7/1983 | Goltz et al. |
| 4,418,048 A | 11/1983 | Dyer et al. |
| 4,435,219 A | 3/1984 | Greigger |
| 4,444,962 A | 4/1984 | McDaniel et al. |
| 4,444,965 A | 4/1984 | McDaniels et al. |
| 4,482,380 A | 11/1984 | Schlegel |
| 4,487,862 A | 12/1984 | Maruya |
| 4,505,954 A | 3/1985 | Hokamura et al. |
| 4,518,513 A | 5/1985 | Lochner et al. |
| 4,542,001 A | 9/1985 | Iino et al. |
| 4,547,479 A | 10/1985 | Johnson et al. |
| 4,567,152 A | 1/1986 | Pine |
| 4,597,796 A | 7/1986 | Ernst et al. |
| 4,622,371 A | 11/1986 | McDaniel |
| 4,640,964 A | 2/1987 | Johnson et al. |
| 4,673,663 A | 6/1987 | Magnier |

(Continued)

FOREIGN PATENT DOCUMENTS

| | | |
|---|---|---|
| BR | 9104581 A | 4/1993 |
| BR | 9400746 A | 10/1995 |
| BR | 9500522 A | 3/1997 |
| EP | 0116865 A1 | 8/1984 |
| EP | 0253663 A2 | 1/1988 |
| EP | 0492137 | 7/1992 |
| EP | 0598464 A1 | 5/1994 |
| EP | 0722660 A2 | 7/1996 |
| EP | 0837031 A2 | 4/1998 |
| EP | 1241131 A1 | 9/2002 |
| EP | 1807475 | 7/2007 |
| FR | 2157866 A1 | 6/1973 |

(Continued)

OTHER PUBLICATIONS

International Search report mailed on Sep. 13, 2013 for PCT/US2013/036499, 3 pages.

(Continued)

*Primary Examiner* — Kriellion Sanders
(74) *Attorney, Agent, or Firm* — Snell & Wilmer L.L.P.

(57) ABSTRACT

Antimicrobial chemical compositions comprise an aluminum phosphate (AlP) solid dispersed within a binding polymer, wherein one or more bioactive materials are disposed within AlP forming a bioactive-AlP complex. The complex may comprise the bioactive material chemically bonded with the AlP, physically combined with the AlP, or a combination of both. The complex may be formed according to precipitation, condensation and sol-gel methods of forming. The complex is engineered to provide a controlled delivery of the bioactive material or a constituent thereof upon exposure to moisture to give a desired level of antimicrobial resistance to a film or composite formed from the composition of at least about 30 $\mu g/m^2$, and may also provide a desired degree of corrosion resistance through the release of passivating phosphate anion. Such antimicrobial chemical compositions provide an improved degree of active, long-term resistance to a broad range of micro-organisms when compared to known antimicrobial chemical compositions.

34 Claims, No Drawings

(56) References Cited

U.S. PATENT DOCUMENTS

| | | |
|---|---|---|
| 4,717,701 A | 1/1988 | McDaniel |
| 4,743,572 A | 5/1988 | Angevine et al. |
| 4,746,568 A | 5/1988 | Matsumoto et al. |
| 4,758,281 A | 7/1988 | Eckler et al. |
| 4,767,802 A | 8/1988 | Sakakibara et al. |
| 4,775,585 A | 10/1988 | Hagiwara et al. |
| 4,782,109 A | 11/1988 | DuLaney et al. |
| 4,876,097 A | 10/1989 | Autant et al. |
| 4,888,056 A | 12/1989 | van der Kolk et al. |
| 4,898,660 A | 2/1990 | Wilson et al. |
| 4,911,898 A | 3/1990 | Hagiwara et al. |
| 4,911,899 A | 3/1990 | Hagiwara et al. |
| 4,959,268 A | 9/1990 | Hagiwara et al. |
| 4,972,002 A | 11/1990 | Volkert |
| 4,990,217 A | 2/1991 | Philippot et al. |
| 4,996,103 A | 2/1991 | Henn et al. |
| 5,028,684 A | 7/1991 | Neuhaus et al. |
| 5,077,332 A | 12/1991 | Blattler et al. |
| 5,096,933 A | 3/1992 | Volkert |
| 5,108,755 A | 4/1992 | Daniels et al. |
| 5,158,610 A | 10/1992 | Bittner |
| 5,183,656 A | 2/1993 | Uesaka et al. |
| 5,208,271 A | 5/1993 | Gallagher |
| 5,242,744 A | 9/1993 | Schryer |
| 5,256,253 A | 10/1993 | Zidovec et al. |
| 5,296,027 A | 3/1994 | Ernst et al. |
| 5,374,411 A | 12/1994 | Davis et al. |
| 5,403,519 A | 4/1995 | Rittler |
| 5,486,232 A | 1/1996 | Griffith et al. |
| 5,488,016 A | 1/1996 | Rittler |
| 5,496,529 A | 3/1996 | Fogel et al. |
| 5,534,130 A | 7/1996 | Sekhar |
| 5,698,758 A | 12/1997 | Rieser et al. |
| 5,707,442 A | 1/1998 | Fogel et al. |
| 5,730,995 A | 3/1998 | Shirono et al. |
| 5,763,015 A | 6/1998 | Hasui et al. |
| 5,783,510 A | 7/1998 | Kida et al. |
| 5,883,200 A | 3/1999 | Tsuchiya et al. |
| 6,002,513 A | 12/1999 | Goossen et al. |
| 6,010,563 A | 1/2000 | Taketani et al. |
| 6,022,513 A | 2/2000 | Pecoraro et al. |
| 6,071,542 A | 6/2000 | Tanimoto et al. |
| 6,117,373 A | 9/2000 | Kida et al. |
| 6,139,616 A | 10/2000 | Nagayama et al. |
| 6,177,489 B1 | 1/2001 | Okuse et al. |
| 6,316,532 B1 | 11/2001 | Nozaki et al. |
| 6,342,546 B1 | 1/2002 | Kato et al. |
| 6,409,951 B1 | 6/2002 | Inoue et al. |
| 6,447,741 B1 | 9/2002 | Chester et al. |
| 6,461,415 B1 | 10/2002 | Sambasivan et al. |
| 6,503,304 B2 | 1/2003 | Korn et al. |
| 6,547,870 B1 | 4/2003 | Griessmann et al. |
| 6,562,474 B1 | 5/2003 | Yoshimi et al. |
| 6,585,989 B2 | 7/2003 | Herbst et al. |
| 6,589,324 B2 | 7/2003 | Kamo et al. |
| 6,635,192 B1 | 10/2003 | Schwarz |
| 6,646,058 B1 | 11/2003 | Koger |
| 6,669,816 B1 | 12/2003 | Poch et al. |
| 6,677,053 B2 | 1/2004 | Yamaji et al. |
| 6,749,769 B2 | 6/2004 | Gai |
| 6,784,236 B2 | 8/2004 | Sugita et al. |
| 6,797,155 B1 | 9/2004 | Chester et al. |
| 6,822,034 B2 | 11/2004 | Hanke et al. |
| 6,838,506 B2 | 1/2005 | Nakao et al. |
| 6,881,782 B2 | 4/2005 | Crater et al. |
| 7,101,820 B2 | 9/2006 | Gai |
| 7,311,944 B2 | 12/2007 | Sambasivan et al. |
| 7,438,881 B2 | 10/2008 | Staffel et al. |
| 7,833,342 B2 * | 11/2010 | Sambasivan et al. ......... 106/474 |
| 2001/0031316 A1 | 10/2001 | Nozaki et al. |
| 2002/0031679 A1 | 3/2002 | Yano et al. |
| 2002/0040557 A1 | 4/2002 | Felton |
| 2002/0158230 A1 | 10/2002 | Bortnik |
| 2003/0113486 A1 | 6/2003 | Sakai et al. |
| 2003/0138673 A1 | 7/2003 | Sambasivan et al. |
| 2004/0011245 A1 | 1/2004 | Sambasivan et al. |
| 2004/0063815 A1 | 4/2004 | Kinose et al. |
| 2004/0071887 A1 | 4/2004 | Newton |
| 2004/0092637 A1 | 5/2004 | McClanahan |
| 2004/0138058 A1 | 7/2004 | Sambasivan et al. |
| 2004/0261909 A1 | 12/2004 | Hamada |
| 2005/0106384 A1 | 5/2005 | Sambasivan et al. |
| 2006/0045831 A1 | 3/2006 | Galembeck et al. |
| 2006/0057407 A1 | 3/2006 | Sambasivan et al. |
| 2006/0211798 A1 | 9/2006 | Galembeck et al. |
| 2008/0035021 A1* | 2/2008 | Sambasivan et al. ...... 106/286.5 |
| 2008/0038556 A1 | 2/2008 | Galembeck et al. |
| 2008/0085965 A1 | 4/2008 | Imakita et al. |
| 2009/0064893 A1 | 3/2009 | Sambasivan et al. |
| 2009/0149317 A1 | 6/2009 | Stamires et al. |
| 2009/0217841 A1 | 9/2009 | Galembeck et al. |
| 2010/0180801 A1 | 7/2010 | Thauern et al. |
| 2010/0203318 A1 | 8/2010 | Galembeck et al. |
| 2012/0091397 A1 | 4/2012 | Foscante |
| 2012/0094130 A1 | 4/2012 | Foscante et al. |

FOREIGN PATENT DOCUMENTS

| | | |
|---|---|---|
| GB | 1403242 A | 8/1975 |
| GB | 2038791 A | 7/1980 |
| JP | 53019345 A | 2/1978 |
| JP | 53059725 A | 5/1978 |
| JP | 55160059 A | 12/1980 |
| JP | 56032553 A | 4/1981 |
| JP | 56032554 A | 4/1981 |
| JP | 56032555 A | 4/1981 |
| JP | 56032556 A | 4/1981 |
| JP | 56131671 A | 10/1981 |
| JP | 57158267 A | 9/1982 |
| JP | 60215091 A | 10/1985 |
| JP | 61101566 A | 5/1986 |
| JP | 61286209 A | 12/1986 |
| JP | 62004753 A | 1/1987 |
| JP | 63101454 A | 5/1988 |
| JP | 1110567 A | 4/1989 |
| JP | 1167381 A | 7/1989 |
| JP | 1234475 A | 9/1989 |
| JP | 1249683 A | 10/1989 |
| JP | 4090874 A | 3/1992 |
| JP | H04243908 A | 9/1992 |
| JP | H05229911 A | 9/1993 |
| JP | 6179866 A | 6/1994 |
| JP | 6286054 A | 10/1994 |
| JP | 7241954 A | 9/1995 |
| JP | 7330451 A | 12/1995 |
| JP | 8072197 A | 3/1996 |
| JP | H08157316 A | 6/1996 |
| JP | 8268704 A | 10/1996 |
| JP | 8283619 A | 10/1996 |
| JP | 10139923 A | 5/1998 |
| JP | 10-213374 A | 8/1998 |
| JP | 10235782 A | 9/1998 |
| JP | 11047261 A | 2/1999 |
| JP | 2001089127 A | 4/2001 |
| JP | 2001158829 A | 6/2001 |
| JP | 2001329221 A | 11/2001 |
| WO | WO-2006024959 A2 | 3/2006 |
| WO | 2008128896 A2 | 10/2008 |

OTHER PUBLICATIONS

Written Opinion of the International Searching Authority mailed on Sep. 13, 2013 for PCT/US2013/036499, 9 pages.

International Search report mailed on Sep. 16, 2013 for PCT/US2013/036672, 4 pages.

Written Opinion of the International Searching Authority mailed on Sep. 16, 2013 for PCT/US2013/036672, 9 pages.

Faison et al.; Use of Polyphosphates as Deflocculants of Alumina; Ceramic Engineering & Science Proceedings; vol. 12[1-2]; 1991; pp. 106-115.

Beppu, M.M., Lima, E. C.O., and Galembeck, F., Aluminum Phosphate Particles Containing Closed Pores: Preparation, Characterization, and Use as a White Pigment, Journal of Colloid and Interface Science 178, 93-103 (1996), Article No. 0097.

(56) References Cited

OTHER PUBLICATIONS

Beppu, M. M., Lima, E. C. O., Sassaki, R.M., and Galembeck, F., Self-Opacifying Aluminum Phosphate Particles for Paint Film Pigmentation, Journal of Coatings Technology, vol. 69, No. 867, 81-88, Apr. 1997.

Lima, E. C. O., Beppu, M. M., Galembeck, F., Filho, J. F. V., and Soares, D. M., Non-Crystalline Aluminum Polyphosphates: Preparation and Properties, J. Braz. Chem. Soc., vol. 7, No. 3, 2009-215, 1996, printed in Brazil.

Souza, E. F., and Galembeck, F., Formation of Opaque Films by Biomimetic Process, Journal of Material Science 32 (1997) 2207-2213.

Dos Santos, R. R. A. C. M. A. and Galembeck, F., Hydrous Non-Crystalline Phosphates: Structure, Function and a new White Pigment, J. Braz. Chem. Soc., vol. 17, No. 8, 1465-1472, 2006, printed in Brazil, XP-002432072.

Souza, E.F., Silva, M. D. C., and Galembeck, F., Improved Latex Film—Glass Adhesion Under Wet Environments by Using and Aluminum Polyphosphate Filler, [publication], 358-377 (1998).

Monteiro, V. A. R., Souza, E. F., Azevedo, M. M. M., and Galembeck, F., Aluminum Polyphosphate Nanoparticles: Preparation, Particle Size Determination, and Microchemistry, Journal of Colloid and Interface Science 217, 237-248 (1999), Article ID jcis.1999.6381, http://www.idealibrary.com.

Burrell, L. S., Johnston, C.T., Schulze, D. Klein, J. White, J. L. and Hem, S. L., Aluminium Phosphate Adjuvants Prepared by Precipitation at Constant pH. Part I: Composition and Structure, Vaccine 19 (2001) 275-281.

Burrell, L.S., Johnston, C.T., Schulze, D. Klein, J. White, J. L. and Hem, S. L., Aluminium Phosphate Adjuvants Prepared by Precipitation at Constant pH. Part II: Physicochemical Properties, Vaccine 19 (2001) 282-287.

Yang, H., Walton, R. I., Biedasek, S., Antonijevic, S., and Wimperis, S., Experimental Observations of Water—Framework Interactions in a Hydrated Microporous Aluminum Phosphate, J. Phys. Chem. B. 2005, 109, 4464-4469.

Filho, P.P.A., and Galembeck, F., Genesis of a Solid Foam: Iron (III) Metaphosphate Transformation in Sol-Gel Crystallization Processes, Langmuir 1990, 6, 1013-1016.

Lima, E. C. O., and Galembeck, F., Particles of Aluminum Metalphosphate Containing Closed Pores. Preparation, Characterization and Optical Properties, Colloids and Surfaces A: Physicochemical and Engineering Aspects, 75 (1993) 65-74.

White Pigment prodn.—by mixing aq. Solns. of metal phosphate, sodium phosphate and ammonium hydroxide, drying the ppte., milling, sievning and igniting: Derwent; 1993; XP002368265; abstract.

Rosetto R et al.; Hydrous non-crystalline phosphates: structure, function and a new white pigment; J. Braz. Chem. Soc., Sao Paulo, BR; vol. 17, No. 8; Jun. 2006; pp. 1465-1472; XP002432072; ISSN: 0103-5053.

Raj, Gurdeep, "Advanced Physical Chemistry" 2009, Krishna Prakashan Media, 35th Edition, pp. 217-220.

Aziz, Z; Abu, SF; Chong, NJ. "A systematic review of silver-containing dressings and topical silver agents for burn wounds." Journal of the International Society for Burn Injuries, 38, issue 3, p. 307-318 (2012).

Storm-Verloot, MN; Vos, CG; Ubbink, DT; Vermuelen, H. "Topical silver for preventing wound infection (Review)." Cochrane database for systematic reviews (on line), Cochrane Library, 2010, issue 3, p. 1-114.

Guggenbichler, JP; Boswald, M; Lugauer, S; Krall, T. "A new technology of microdispersed silver in polyurethane induces antimicrobial activity in central venous catheters." Infection, 27 Supplement 1, S16-S23, (1999).

Lok, CN; Ho, CM; Chen, RC; He, QY; Sun, H; Tam, PK; Che, CM; "Silver nanoparticles: partial oxidation and antibacterial activities." Journal of Biological Inorganic Chemistry (2007) 12:527-534.

Prabhu, S; Poulose, E; "Silver nanoparticles: mechanism of antimicrobial action, synthesis, medical applications, and toxicity effects." International Nano Letters 2012, 2:32.

Egger, S; Lehmann, RP; Height, MJ; Loessner, MJ; Schuppler, M. "Antimicrobial properties of a novel silver-silica nanocomposite material." Applied Environmental Microbiology, 2009, 75(9), p. 2973-2976].

Sondi, I; Salopek-Sondi, B. "Silver nanoparticles as antimicrobial agent: a case study on $E.\ coli$ as a model for gram-negative bacteria." Journal of Colloid and Interface Science 275 (2004) 177-182].

Kawahara, K; Tsuruda, K; Morishita, M; Uchida, M. "Antibacterial effect of silver zeolite on oral bacteria under anaerobic conditions." Dental Materials, 2000, vol. a6, issue 6, p. 452-455].

Felipe Lagno and George P. Demopoulos, Synthesis of Hydrated Aluminum Phosphate, AlPO4-1.5H20 (AIP04-H3), by Controlled Reactive Crystallization in Sulfate Media, Ind. Eng. Chem. Res., vol. 44, No. 21, 2005, pp. 8033-8038, American Chemical Society, Published on Web Sep. 10, 2005, IE0505559.

\* cited by examiner

ANTIMICROBIAL CHEMICAL COMPOSITIONS

FIELD OF THE INVENTION

This invention relates to chemical compositions having antimicrobial properties and, more specifically, to chemical compositions that are specially formulated to include an aluminum phosphate complex comprising one or more antimicrobial agents, and methods for making the same.

BACKGROUND OF THE INVENTION

Chemical compositions formulated to include one or more antimicrobial agents to provide antimicrobial properties, e.g., provided in the form of a coating composition or the like for forming a film layer on an underlying substrate surface, are known in the art. Such antimicrobial chemical compositions make use of antimicrobial agents known to provide some degree of protection against unwanted micro-organisms.

Conventional antimicrobial chemical compositions known in the art, e.g., formulated products such as water-based paints and coatings, include biocides incorporated therein to preserve the liquid composition during storage from spoilage by micro-organisms. Antimicrobial protection is afforded from such conventional paints and coatings by the incorporation of agents that prevent defacement of the applied, dry film in service by mold and/or mildew growth.

While conventional antimicrobial chemical compositions are known to provide some protection against unwanted microorganisms, the protection afforded is somewhat limited in both the degree of its activity, and the length in time of its being able to offer a desired level of resistance to unwanted microorganisms. This is largely due to the nature of the formulation and the limited activity of the antimicrobial agent disposed therein, and the resulting inability to provide a highly-active and long-lasting resistance to unwanted microorganisms. Thus, while such conventional antimicrobial chemical compositions are capable of providing some degree of resistance to microorganisms, they are unable to provide a desired or needed level of microorganisms control sufficient to meet the demands of certain end-use applications.

There is an unmet need to provide active, long-term resistance to a broad range of bacteria, mold, mildew, and other harmful micro-organisms to prevent collateral effects of illness and/or product spoilage due to infection. Examples of target end-use applications where it is critical to prevent infection and product spoilage from surface contact in sensitive environments includes: hospitals and health care facilities; kitchens and food processing and storage areas; dairies; breweries; bathroom and rest room facilities; hotels; school, recreation, amusement, and sports facilities. While existing anti-microbial additives may provide some degree of anti-microbial action, their effectiveness in such formulated products as paints and coatings is limited by the amounts of material required to achieve anti-microbial action, which exceeds: (1) cost constraints for the formulated product; (2) usage limitations relative to non-target toxicity; (3) the practical limits for incorporation in the formulated product; and (4) which may be limited by the mechanism for delivery to the surface of the article to be protected.

It is, therefore, desired that antimicrobial chemical compositions be formulated in a manner that provide a desired active, long-term resistance to a broad range of micro-organisms, including bacteria, mold, mildew, and other microbiological species to prevent collateral effects of illness and product spoilage, when compared to known antimicrobial chemical compositions, thereby meeting the needs of certain end-use applications. It is desired that such antimicrobial chemical compositions be engineered in a manner facilitating the ability to effectively customize, adjust and/or tailor changes in the performance characteristics of the formulations for the purpose of effectively addressing the specific antimicrobial needs associated with different end-use applications. It is further desired that such antimicrobial chemical compositions be formulated from readily available materials, and/or be made by methods, that facilitate manufacturing the chemical compositions in a manner that does not require the use of exotic equipment, that is not unduly labor intensive, and that is economically feasible.

SUMMARY OF THE INVENTION

Antimicrobial chemical compositions as described herein generally comprise an aluminum phosphate (AlP) solid that is dispersed within a binding polymer. One or more bioactive materials are disposed within or combined with the AlP to form a bioactive-AlP complex. A feature of the complex is that it is specifically engineered such that, when the composition is provided in the form of a dried film or composite, it provides a controlled delivery of a bioactive constituent (derived from the bioactive material upon exposure to moisture) to the film or composite surface to provide a desired level of antimicrobial resistance. The AlP used to form the complex may be in amorphous form, in crystalline form, or in a combination thereof. In an example embodiment, the AlP comprises amorphous AlP.

The bioactive material or a bioactive constituent derived therefrom, used to form the complex may either be chemically bonded with, e.g., provided in the backbone of, the AlP polymer, or may be physically incorporated, enmeshed, encapsulated, or intertwined with the AlP polymer, depending on the particular method used to make the complex. The bioactive material can be organic and/or can be a metal salt or oxide such as those including silver salts, copper salts, zinc salts, calcium salts, and combinations thereof, and/or can be a metal ion such as those including silver, copper, zinc, calcium, and combinations thereof. Binding polymers used to form the composition can include polyurethanes, polyesters, solvent-based epoxies, solventless epoxies, water-borne epoxies, epoxy copolymers, acrylics, acrylic copolymers, silicones, silicone copolymers, polysiloxanes, polysiloxane copolymers, alkyds and combinations thereof.

In an example embodiment, the AlP is engineered to provide a controlled delivery of the bioactive constituent when the chemical composition is in a cured form, e.g., in the form of a coating film or a composite structure, of from about 5 to 1,000 ppm, preferably about 10 to 900 ppm, and most preferably from about 15 to 800 ppm. In an example embodiment, it is desired to provide at controlled delivery of at least 100 ppm or greater of the bioactive constituent. The amount of the bioactive material, e.g., Ag, in the complex may be in the range of from about 1 to 10 percent by weight, preferably from about 2 to 8 percent by weight, and more preferably from about 3 to 6 percent by weight based on the total weight of the complex. The ratio of phosphate to aluminum in the complex is in the range of from about 0.5:1 to 1.5:1. The bioactive-AlP complex in the chemical composition comprises from about 0.1 to 2 percent of the dry film weight, or 20 to 1,000 ppmw of bioactive constituent, e.g., Ag in the paint. In a preferred embodiment, an effective leaching rate, that is, amount of bioactive constituent, e.g., Ag, released on the surface of a cured coating or cured composite comprising the bioactive-AlP complex is at least about 30 µg/m², and is preferably about 36.9 µg/m² or >2 µg/L in a rinse for bioactivity.

In an example embodiment, the antimicrobial chemical composition may also provide a desired degree of corrosion resistance, e.g., when formulated as a coating for use with metallic substrates. In such embodiment, the AlP is formulated to provide, in addition to the controlled release/delivery of bioactive constituent, a controlled delivery of passivating anion such as phosphate anion upon exposure to moisture. In an example embodiment, such antimicrobial chemical composition may provide a controlled delivery of phosphate anion of greater than about 100 ppm.

Antimicrobial chemical compositions as described herein are made by first forming the bioactive-AlP complex, which comprises forming an AlP by combining a desired aluminum source, with a desired phosphate source under suitable reaction conditions, e.g., in an aqueous solution at suitable pH and suitable temperature, to form the AlP. The bioactive material is added to the AlP during and/or after the step of forming the AlP so that the bioactive material is dispersed or combined with the AlP, thereby forming the bioactive-AlP complex. If desired, further AlP can be added to the bioactive-AlP complex before combining the complex with the binding polymer.

According to one example method of making, the bioactive material is added to the AlP after it has been formed, in which case the resulting bioactive-AlP complex comprises the bioactive material physically incorporated, enmeshed, encapsulated, or intertwined with the AlP polymer. According to another example method of making, the bioactive material is added to the AlP during formation of the AlP, in which case the resulting bioactive-AlP complex is formed in-situ with the ALP and comprises a bioactive constituent of the bioactive material chemically bonded to the AlP polymer, e.g., as part of the ALP polymer backbone.

Antimicrobial chemical compositions as described herein are specifically engineered to provide active, long-term resistance to a broad range of micro-organisms, including bacteria, mold, mildew, and other micro-biological species to prevent collateral effects of illness and product spoilage, when compared to known antimicrobial chemical compositions, thereby meeting the needs of certain formulated end-use applications, wherein such applications include paints, coatings, adhesives, composites, cements, plastics and the like. These antimicrobial chemical compositions are made from readily available materials and/or by methods that facilitate manufacturing in a manner avoiding exotic equipment, which is not unduly labor intensive, and that is economically feasible.

DETAILED DESCRIPTION

Antimicrobial chemical compositions as described herein generally comprise an aluminum phosphate (AlP) that is dispersed within a binding polymer that forms the bulk matrix of the composition. One or more bioactive materials are disposed within the aluminum phosphate, thereby forming a bioactive-AlP complex, and the and the aluminum phosphate is specifically engineered to provide controlled delivery or release of a bioactive constituent derived from the bioactive material upon exposure to moisture. Such antimicrobial chemical compositions are made by a number of methods described herein, and can be formulated for use as paints, coatings, adhesives, composites, cements, plastics, and the like.

Aluminum phosphates useful in this regard include amorphous aluminum phosphates, crystalline aluminum phosphate, and combinations thereof. Example aluminum phosphates useful in this regard are amorphous aluminum phosphates (AAlPs), and preferred AAlPs are amorphous aluminum orthophosphates. While the use of AAlPs is desired because AAlPs have been shown to have certain characteristic properties, making them well suited for use as a carrier to the bioactive material, crystalline AlPs and combinations of amorphous and crystalline AlPs are also understood to be useful in this regard and within the scope of the antimicrobial chemical compositions as disclosed herein.

In an example embodiment, the amorphous aluminum orthophosphates are amorphous aluminum hydroxy phosphates. Amorphous aluminum hydroxy phosphates provide uniform dispersion properties within the composition and the dispersion remains stable throughout the shelf-life of the formulation. The hydroxyl content of the amorphous aluminum hydroxy phosphate provides matrix stability by providing hydrogen bonds with suitable groups of the binding polymer of the formulation, e.g., such as carboxyl groups, amino groups, hydroxyl groups, acid groups and the like. This feature is unique to the amorphous aluminum hydroxy phosphate, and is not present in crystalline or other types of amorphous phosphates, and for this reason help to provide uniform dispersion properties AlPs used to form antimicrobial chemical compositions disclosed herein are specially designed to have a high level of compatibility with a variety of different binding polymers or binding polymer systems useful for formulating such end-use applications, thereby providing a high degree of flexibility and choice in formulating such compositions to meet the needs and conditions of a variety of end-use applications in a number of different end-use industries.

Controlled delivery and/or release of the bioactive constituent within the chemical composition is largely dependent on the diffusion rate of the bioactive constituent through the bulk matrix of the composition, whether in the form of a coating or a composite. The diffusion rate of the bioactive constituent is dependent on the structural features of the bulk matrix that control bioactive constituent and water transport. These features include, but are not limited to, cross-link density, pigment to volume ratio (PVC), nature of the bioactive material carrier, hydrophilicity of components, and the polarity of the components.

Antimicrobial chemical compositions as disclosed herein use AlP as the bioactive carrier material, which AlP is engineered to provide a controlled diffusion of both moisture to the bioactive material contained therein, and a diffusion or delivery or release of the bioactive constituent to the surface of a coating or composite comprising such AlP, for purposes of providing a desired degree of antimicrobial resistance. Accordingly, the bioactive material is incorporated into the AlP, which has been specifically made to moderate and control the solubility of the bioactive constituent, and to control the diffusion of the dissolved bioactive constituent through the composition film or composite bulk matrix.

A characteristic/parameter of the AlP discovered to have an influence over the diffusion of moisture and delivery of the bioactive constituent is the porosity of the AlP molecule. A feature of AlP complexes as disclosed herein is the ability to engineer the morphology and the porosity of such complexes by choice of synthesis method. As used herein, the term "engineered porosity" is defined as the volume of space existing within a solid material consisting of particle voids, interstitial space between particles in particle aggregates, and interstitial space between aggregates in agglomerates. Mercury porosimetry is used to characterize the porosity properties of solids and pigments. Key measurements include:

1. Total intrusion volume (ml/g)—measures the overall space in the sample into which mercury can be absorbed as a function of pressure.
2. Total pore area (m$^2$/g)—converts volume to area and defines how much area is occupied by the total intrusion volume.
3. Average pore volume (4 V/A=µ)—shows the distribution of volume by area, i.e., how much volume on the average goes into different pore sizes.
4. BET (m$^2$/g)—is the measure of total surface area accessible to nitrogen gas under test conditions. BET and porosity correlate.

AlP complexes comprising a metal salt or metal ion, e.g., such as silver, as the bioactive material and formed by sol-gel method (as described in better detail below) result in the formation of nano-sized primary particles incorporated into aggregates of very-high surface area and porosity. An advantage of having such high surface area and porosity is that it ensures optimum diffusion contact with water and subsequent release of the silver ion in the film formed by the binding polymer bulk matrix, thereby promoting uniform distribution of the complex throughout the film or composite, and promoting a relatively rapid release of the bioactive material from the complex upon contact with water.

AlP complexes comprising a metal salt or metal ion, e.g., such as silver, as the bioactive material and prepared by the sol-gel method have BET surface areas ranging from about 100 and 250 m$^2$/g, and preferably between about 125 and 200 m$^2$/g, and most preferably between about 140 and 160 m$^2$/g. Such AlP complexes have a total intrusion volume of between about 1 and 2 mL/g, and preferably between about 1.3 and 1.8 mL/g. Such AlP complexes have an average pore volume of from about 0.02 to 0.06 µm, and preferably between about 0.04 and 0.05 µm.

In contrast, AlP complexes comprising a metal salt or metal ion, e.g., such as silver, as the bioactive material and formed by precipitation or condensation method (as described in better detail below) result in the formation of nano-sized primary particles incorporated into aggregates of relatively low surface area and low porosity. An advantage of having low surface area and porosity is that it ensures reduced degree of diffusion contact with water and subsequent release of the silver ion in the film or composite formed by the binding polymer bulk matrix, thereby promoting uniform distribution of the complex throughout the film or composite, and promoting a relatively slow release of the bioactive material from the AlP complex upon contact with water.

AlP complexes comprising a metal salt or metal ion, e.g., such as silver, as the bioactive material and prepared by precipitation or condensation method have BET surface areas ranging from about 2 to 10 m$^2$/g, total intrusion volumes ranging from about 0.5 to 0.9 mL/g, and have average pore volumes ranging from about 0.4 to 0.6 µm.

Thus, a feature of AlPs useful for making antimicrobial chemical compositions is that they have an engineered porosity calculated to provide the desired rates of moisture diffusion and delivery of bioactive constituent that promotes a desired degree of activity and antimicrobial resistance when placed in an end-use application.

Thus, the desired porosity of the AlP is understood to vary depending on the certain requirements called for by each different end-use application. However, it is generally desired that the porosity of the AlP be not so great so as to rapidly extinguish the bioactive constituent upon exposure to moisture, e.g., be highly active but provide a greatly reduced effective service life. The loading of the bioactive material and/or the type of bioactive material that is used will also influence the activity and effective service life. Accordingly, the porosity of the AlP reflects a balance or compromise between a desired degree of antimicrobial activity and a desired effective service life for a given amount or general loading range of a given bioactive material.

The porosity of the AlP is engineered during the process of making the AlP and/or during post formation processing, e.g., drying and/or other heat treatment, as described in greater detail below.

AlPs as disclosed herein, in addition to serving as the bioactive material carrier to provide desired controlled delivery/release of the bioactive constituent, provide anticorrosion protection through the delivery of phosphate anion when exposed to moisture. Accordingly, for those end-use applications calling for both antimicrobial and anticorrosion properties, e.g., in the case where the composition is formulated for use as a coating on a metal substrate, the AlP can also be engineered to provide a controlled delivery of the phosphate anion to provide a desired degree of corrosion protection through passivation to a metal substrate.

In an example embodiment, wherein such corrosion resistance is also desired, the AlP is engineered to release in the range of from about 50 to 500 ppm, and preferably 100 to 200 ppm of the passivating phosphate anion when present in a cured film or composite placed into an end-use application. The amount of passivating anion to be delivered depends on a number of different factors such as the loading or amount of the AlP used, the type of binding polymer that is used, the type of metallic substrate being protected, and the type of environment present in the end-use application. In a preferred embodiment, where the metallic substrate being protected comprises iron and the corrosion environment comprises water, oxygen, and other corrosive salts, the AlP is engineered to release approximately 160 ppm of the passivating phosphate anion.

Example binding polymers include those currently used for making known antimicrobial chemical compositions, and can be selected from the general group including water-borne polymers, solvent-borne polymers, hybrids and combinations thereof. Example water-borne polymers useful for making anticorrosion coating compositions include acrylic and acrylic copolymers, alkyd, epoxy, polyurethane, and silicone, and polysiloxane polymers. Example solvent-borne and/or non-aqueous polymers useful for making anticorrosion coating compositions include acrylic and acrylic copolymers, epoxy, polyurethane, silicone, polysiloxane, polyester, and alkyd. Preferred binding polymers include acrylic copolymer latex, alkyd, polyurethane and epoxy polymers.

In an example embodiment, antimicrobial chemical compositions comprise in the range of from about 15 to 75 weight percent, preferably in the range of from about 20 to 60 weight percent, and more preferably in the range of from about 20 to 35 weight percent of the binding polymer based on the total weight of the chemical composition when in a pre-cured or wet state. An antimicrobial chemical composition comprising less than about 15 percent by weight of the binding polymer may include a greater amount of the bioactive material (present as the bioactive-AlP complex) than necessary to provide a desired degree of antimicrobial protection. An antimicrobial chemical composition comprising greater that about 75 percent by weight of the binding polymer may include an amount of the bioactive material (present as the bioactive-AlP complex) that is insufficient to provide a desired degree of antimicrobial resistance. While certain amounts of the binding polymer have been provided, it is to be understood that the exact amount of the binding polymer that is used to formulate antimicrobial chemical compositions will vary depending on such factors as the type of binding polymer used, the types and amounts of other materials used to form the chemical composition, the type and/or quantity of bioactive material that is used, and/or the particular end-use antimicrobial application.

Bioactive materials or agents useful in forming antimicrobial chemical compositions described herein can be selected from a variety of bioactive materials and/or species including, but not limited to: (1) antimicrobial additives comprising organic molecules that are either biocidal (kill microbes) or biostatic (inactivate microbes); (2) bio-pesticides, typically peptides that have biostatic or biocidal effects on microbes; (3) natural products that inhibit or prevent the growth of the target organisms naturally; (4) "friendly" bacteria that interfere with the growth and/or development of target microbes; (5) minerals and metals that release or produce antimicrobial species in response to certain environmental conditions; and (6) combinations thereof. Organic antimicrobial additives and metal-based biocides have most commonly been used to impart antimicrobial properties to formulated products.

Metal-based materials useful as bioactive materials or agents include metal ions and metal salts. Suitable metal ions include those selected from the group consisting of silver, copper, zinc, calcium, and combinations thereof. Suitable metal salts include salts of the above-identified metal ions. In an example embodiment, silver is a desired bioactive material because it has several advantages, provided that it can be made compatible with the formulation of the binding polymer in which is it incorporated, and provided that the silver can be maintained in an active state within the formulation for delivery to the surface upon exposure to moisture in a consistent and cost effective manner. Silver is advantageous over organic materials because it has higher degree of thermal stability, a lower level of toxicity to non-target organisms than typical organic biocides, and has a higher level of UV stability.

Silver ion ($Ag^+$) is bioactive, and in sufficient concentration kills a variety of microorganisms. Silver has proven anti-microbial activity and is known to be effective against certain antibiotic-resistant bacteria. It has broad spectrum anti-microbial activity and minimal toxicity toward mammalian cells. Silver is typically formulated or incorporated as an active ingredient in a carrier component (at concentration levels typically <5% by weight) such as glass, silica, or zeolite. The mechanism of action by which silver-based materials control micro-organisms involves the release of silver ion in response to ambient moisture. The silver ion is formed by contact with water, and the ion contacts the organism and interacts with multiple binding sites in the organism. As the silver ion is transferred into the cells of the target organism metabolic, the respiratory functions of the cell are altered and eventually cease, causing the cell to die.

Suitable sources of silver for use as the bioactive material include silver salts such a silver nitrate and silver chloride, wherein silver nitrate ($AgNO_3$) is preferred. Silver nitrate is extremely soluble (122 grams per 100 milliliters of water at 0° C.) and this solubility presents a special challenge for controlled delivery of the bioactive material from a formulated product, such as an antimicrobial coating or composite. Silver nitrate is useful as a bioactive material as long as the delivery of silver ion from the formulated coating or composite to the surface is controlled at a rate and in a concentration balanced to supply the minimum control level for the target service life. Too rapid of a delivery will result in excessive concentration of silver ion on the surface to be protected, causing a discoloration of the surface and/or a rapid depletion the available reserves of silver nitrate in the bulk matrix, thereby reducing effective service life.

As discussed above, the AlP is made having an engineered porosity to provide a controlled diffusion rate and release/delivery of the bioactive constituent, e.g., silver ion, through the bulk matrix of the coating or composite. The incorporation of silver nitrate directly into a coating as a free component will not allow for controlled release. It is necessary to incorporate the silver nitrate (or silver ion source) in the AlP as engineered to moderate and control the solubility of the silver salt, control the diffusion of the dissolved silver ion through the film or composite matrix, and to control the resulting delivery of the silver ion to the surface.

As noted above, the porosity properties of AlP are engineered to provide a mechanism to control such reactions as hydrolysis and dissolution. Additionally, the AlP can be made hydroscopic so that it attracts water to itself specifically in a bulk matrix, thereby providing a medium for dissolution interactions. The feature of engineered porosity is the basis for controlled dissolution and ion release. In the case of silver ion, the diffusion rate of silver ion is dependent on the surface area and the porosity of the AlP. This also moderates the overall transport rate of the silver ion through the bulk matrix. Specifically, when water contacts the bulk matrix it is absorbed, and when the water in the bulk matrix contacts the highly soluble silver disposed within the bioactive-AlP complex (either as silver nitrate physically encapsulated within the AlP or as a silver ion chemically bonded to the AlP) the silver species is dissolved and the silver ion undergoes diffusion through the bulk matrix to the surface.

A feature of antimicrobial compositions as disclosed herein is that such compositions comprise the use of the AlP complex disposed within the bulk matrix of the binder polymer, wherein the AlP complex has a rate of bioactive constituent delivery that can be the same or different than the rate of bioactive constituent (released from the complex) migration or diffusion through the binder polymer. Thus, a formulator can engineer the porosity of the AlP complex to provide a desired release rate of the bioactive constituent therefrom, and can further engineer the formulation (by use of different binding polymers, fillers and the like) to influence the migration or diffusion rate of the bioactive constituent through the composition to meet certain end-use application demands. The combination of these features, i.e., the release rate of the bioactive constituent from the AlP complex, and the migration or diffusion rate of such released bioactive constituent through the binder polymer bulk matrix, provide for an enhanced level of antimicrobial composition customization not otherwise available. Such customization of release rates and migration/diffusion rates operate to provide a vast range of antimicrobial compositions that can be specifically tailored to address a variety of end-use applications.

The amount or concentration of the bioactive material that is incorporated into the AlP can and will vary depending on such factors as the type of bioactive material used, the nature of the binding polymer used to form the coating or composite matrix, the type of AlP (amorphous, crystalline, or a combination thereof), and the engineered porosity of the AlP. Thus, the properties of the bioactive-AlP complex, such as the bioactive material concentration and the AlP engineered porosity can be controlled to address various exposure conditions such as temperature, relative humidity, ultra-violet exposure and the like.

In an example embodiment, it is desired that a sufficient amount of the bioactive material be present, and that the AlP have an engineered porosity that will result in the composition, when provided in the form of a dried film or composite, to provide a controlled delivery of the bioactive constituent (derived from contacting the bioactive material with moisture) of from about 5 to 1,000 ppm, preferably of from about 10 to 900 ppm, and more preferably in the range of from about 15 to 800 ppm. In a particular embodiment, where the bioactive constituent is silver ion, a desired optimum controlled delivery of the silver ion is greater than about 100 ppm, and most preferably about 120 ppm. In a preferred embodiment, an effective leaching rate, that is, amount of bioactive constituent, e.g., Ag, released on the surface of a cured coating or cured composite comprising the bioactive-AlP complex is at least about 30 µg/m$^2$, and is preferably about 36.9 µg/m$^2$ or >2 µg/L in a rinse for bioactivity.

In order to provide the desired controlled delivery of the bioactive constituent, it is desired that certain amount of the bioactive material be used when forming the bioactive-AlP complex. In an example embodiment, the AlP complex comprises from about 1 to 10 percent by weight of the bioactive material, preferably from about 2 to 8 percent by weight of the bioactive material, and more preferably from about 3 to 6 percent by weight of the bioactive material based on the total weight of the bioactive-AlP complex.

Additionally, it has been discovered that mixed anti-microbial complexes based on silver and other bio-active materials can be synthesized which have synergistic effects. For example, in addition to silver-ALP complexes, other bioactive metals as copper and/or zinc can be introduced into the complex by their inclusion in the synthesis process as better described below. Further, certain organic bio-active molecules can be introduced into the complex through physical adsorption/encapsulation or by actual reaction/condensation with the phosphate group of the complex. This provides a controlled release mechanism through subsequent hydrolysis in the bulk film by the diffusion of water.

AlPs can be made through the selective combination the materials noted above. The following selected methods of preparation are provided below as examples, and it is to be understood that other methods of preparation other than those specifically disclosed may be used. While the methods disclosed herein for making AlPs may reference and disclose the formation of amorphous aluminum phosphate (AAlP), it is to be understood that such methods may also produce or be adapted to produce other forms of AlP, such as the various crystalline aluminum phosphate forms and/or mixtures of amorphous and crystalline aluminum phosphates, depending on the end-use antimicrobial application performance properties. Example crystalline forms of AlPs formed as disclosed herein include and are not limited to orthorhombic and triclinic aluminum orthophosphates. Accordingly, the methods disclosed herein are understood to be useful for making different forms of AP, depending on the particular end-use applications and performance properties.

Binary Condensation Methods of Making

Generally, the AlP is an aluminum phosphate complex that is prepared by combining a suitable aluminum salt, such as aluminum hydroxide, aluminum sulfate and the like with phosphoric acid or other phosphorus-containing compound or material, depending on the particular type of aluminum salt selected for forming the aluminum phosphate. In an example embodiment, a preferred aluminum salt is aluminum hydroxide (Al(OH)$_3$), and a preferred source of the phosphorus-containing ingredient is phosphoric acid (H$_3$PO$_4$). Example methods as disclosed herein comprise forming AlP by a condensation process, wherein the AlP is formed by the condensation reaction of the aluminum salt ingredient with the phosphorous-containing ingredient to produce AlP particles in slurry form. The composition of the condensed solid resulting from such process of making depends on the ratio of the aluminum metal to phosphate anion. The properties of the resulting complex, i.e., the AlP, depends on the processing parameters employed during the condensation reaction, including choice of aluminum salt, temperature, the physical state of the reactants, order of addition of reactants, rate of addition of reactants, the degree and duration of agitation, pretreatment of one or more of the reactants, and post treatment of the resulting condensation product.

Generally speaking, the condensed solid that results from this method of making, even after milling, has a very low oil absorption property and low surface area (as measured by BET method) when compared to aluminum phosphate prepared by other known methods. Oil absorption is defined as the amount (grams or pounds) of linseed oil required to wet out and fill the voids spaces around a pigment, ASTM-D-281-84, which is a measure of the binder demand or the amount of binder resin that a pigment may absorb in a given formulation. High binder demand adds to formulation cost and can affect certain barrier properties of the dry film. This is further surprising because the aluminum phosphate made by the binary condensation process disclosed herein also displays the controlled release property and water adsorption property usually associated with high surface area particles.

In an example embodiment, the condensed aluminum phosphate prepared herein has an oil absorption of less than about 50, preferably in the range of between about 10 to 40, and more preferably in the range of between about 20 to 30. In contrast, AlP that is made by other methods has an oil absorption of greater than about 50, and typically in the range of about 50 to 110.

In an example embodiment, the AlP prepared herein has a surface area of less than about 20 m$^2$/g, and preferably less than about 10 m$^2$/g. In an example embodiment, the surface area is in the range of between about 2 to 8 m$^2$/g, and more preferably in the range of between about 3 to 5 m$^2$/g. In contrast, AlP made by other methods has a surface area greater than 20 m$^2$/g, e.g., from about 30 to 135 m$^2$/g.

AlPs made as a binary condensation product can be produced according to least five different methods, wherein two of which involve adding a base reactant to an acid reactant, one of which involves adding an acid reactant to a base reactant, one of which involves base-to-acid in-situ aggregation, and one of which involves acid-to-base in-situ aggregation. In such methods, selected starting materials including an aluminum source and a phosphorous source are combined under specific conditions of controlled material delivery, temperature, and agitation. The judicious selection of starting materials and processing conditions produces AlPs having a material content and chemical structure intentionally created with the purpose of producing the above-noted engineered characteristics to provide the desired controlled delivery/release of the bioactive constituent when formulated into a coating composition or composite.

As noted above, aluminum sources useful for forming AlP by binary condensation method include aluminum salts, such as aluminum hydroxide, aluminum chloride, aluminum nitrate, aluminum sulfate, and the like. Preferred aluminum sources include aluminum hydroxide and aluminum sulfate. Phosphorous sources useful for forming AlP by condensation include phosphoric acid, and salts of phosphorus as orthophosphates or as polyphosphates. A suitable source of phosphorus is fertilizer grade phosphoric acid, from any origin, that has been clarified and discolored. For example, a commercial phosphoric acid containing approximately 54% of $P_2O_5$ may be chemically treated and/or diluted with treated water resulting in a concentration of approximately 20% of $P_2$.

AlPs useful for forming antimicrobial chemical compositions described herein can be made according to a number of different methods, which includes at least five variations of the binary condensation process. The following selected methods of preparation are provided below as examples, and it is to be understood that other methods of preparation other than those specifically disclosed may be used.

Example No. 1

Binary Condensation Formation of the AlP
(Base-to-Acid Route)

In an example embodiment, AlP is prepared by adding aluminum hydroxide ($Al(OH)_3$) to phosphoric acid ($H_3PO_4$). The $H_3PO_4$ was diluted with water before being combined with the $Al(OH)_3$ and, prior to addition, the $Al(OH)_3$ was not wetted with water, although wetted $Al(OH)_3$ can be used. The reactants were quickly combined at room temperature without heating to produce a white slurry. However, if desired, the reaction can be heated. The $H_3PO_4$ was 85 wt % in water provided by Sigma-Aldrich, and the $Al(OH)_3$ was reagent grade provided by Sigma-Aldrich. Specifically, approximately 57.3 g (0.5 mole) $H_3PO_4$ was diluted with 50 g of water before being combined with $Al(OH)_3$. Approximately 39 g (0.5 mole) of $Al(OH)_3$ was added to the solution quickly and the mixture was stirred slowly at room temperature to wet the powder. An AlP condensed solid was formed and existed as a dispersion of solid AlP particles in water. In this particular embodiment, the AlP particles existed primarily in the form of amorphous aluminum phosphate (AAlP). Diluting the $H_3PO_4$ prior to addition of the $Al(OH)_3$ thereto is believed to contribute to forming exclusively AAlP, e.g., wherein there is little to no crystalline form produced. The suspension was filtered to isolate the AlP particles. The particles were washed and dried to an appropriate temperature, which may be less than about 300° C., and preferably from about 100° C. to 200° C. A feature of the AlP so formed is that it may be combined with a binding polymer, e.g., used for formulating an antimicrobial coating composition, without the need for further heat treatment, tempering, or calcining. While heating the AlP at the extreme temperatures noted above may be useful for driving off water, such may also initiate conversion of the AlP from an amorphous form to a crystalline form. It may be desired to subject the AlP to elevated temperatures above 200° C., e.g., of between 300° C. to 800° C., to either remove unwanted constituents therefrom and/or to influence physical characteristics of the AlP that may influence its end-use performance properties or characteristics in the antimicrobial composition. If a crystalline form of AlP is desired, the AlP so formed can be further heat treated or calcined to produce the desired crystalline AlP.

Alternatively, the AlP was prepared by adding the $Al(OH)_3$ to the $H_3PO_4$. However, unlike the example embodiment disclosed above, the $H_3PO_4$ was not diluted before combining with the $Al(OH)_3$. However, before combining, the $H_3PO_4$ was heated. Additionally, prior to combining with the $H_3PO_4$, the $Al(OH)_3$ was wetted with water. A feature of this method of preparing is that it does not include the addition of free water after combination of the reactants, although it is to be understood that the AlP can be made according to this method by including the addition of free water. In an example embodiment, the $H_3PO_4$ was 85 wt % in water provided by Sigma-Aldrich, and the $Al(OH)_3$ was reagent grade provided by Sigma-Aldrich. Specifically, approximately 57.6 g $H_3PO_4$ was heated to a temperature of about 80° C. Approximately 39 g of $Al(OH)_3$ was wetted with about 2 g water and the wetted $Al(OH)_3$ was quickly added to the $H_3PO_4$ under fast mechanical stirring. An AALP solid was formed and existed as a dough-like ball that was removed and stored at room temperature. A feature of the AlP so formed is that further treatment in the form of filtering and washing was not necessary to isolate and obtain the desired AlP. Like the example embodiment disclosed above, such AlP was dried and formed into the desired particle size useful for forming the antimicrobial chemical composition.

Example No. 2

Binary Condensation Formation of the AlP
(Base-to-Acid Route)

In an example embodiment, AlP having the above-noted engineered physical properties or characteristics, e.g., porosity, is prepared by adding aluminum hydroxide ($Al(OH)_3$) to phosphoric acid ($H_3PO_4$) at an elevated temperature, e.g., at about 60° C., to form the desired AlP. The $H_3PO_4$ was diluted with water before being combined with the $Al(OH)_3$ and, prior to addition, the $Al(OH)_3$ was combined with water to form a slurry comprising between about 10 to 25 percent by weight, and in some cases up to about 40 percent by weight $Al(OH)_3$, depending on the grade of the $Al(OH)_3$. In preparing the $Al(OH)_3$ slurry, the water may be heated to facilitate dispersion of the aluminum hydroxide powder, e.g., to overcome certain properties of a specific grade of aluminum hydroxide. The heated slurry may be maintained at an elevated temperature and added to the acid. With very high-grade aluminum hydroxide, having a high degree of purity and small particle size and distribution, the $Al(OH)_3$ slurry can be made by adding to room temperature water.

The $Al(OH)_3$ slurry was added slowly to the diluted $H_3PO_4$ for the purpose of controlling the kinetics of the condensation reaction. In an example embodiment, the $Al(OH)_3$ slurry was added in a controlled manner, e.g., in a drop-wise fashion or the like, to the $H_3PO_4$ over a period of approximately 10 minutes to about one hour. The combined reactants were heated to a temperature of approximately 95° C., and the reactants were mixed together for a sufficient period of time, typically about 3 hours. In an example embodiment, the reaction takes place in a constant volume system that is essentially closed, e.g., a reflux condenser may be attached to maintain constant solvent volume (water) in the reaction system. In an example embodiment, the $H_3PO_4$ was 85 wt % in water provided by Sigma-Aldrich, and the $Al(OH)_3$ was reagent grade, provided by Sigma-Aldrich. Specifically, approximately 864 g of 85% dilute $H_3PO_4$ was used, and the slurry was formed by combining 585 g of $Al(OH)_3$ with 1,650 g of deionized water. The combined reactants were contained in a mixing vessel and mixed at 1,300 to 1,500 rpms. Further water was added to the reactants and the combination was mixed for approximately 30 minutes to about 3 hours, e.g., more typically the latter.

If desired, a suitable chemical agent can be added to the reactants for the purpose of reducing the solubility of the components of the mother liquor, thereby providing still further increased control over the outcome of the reaction. In an example embodiment, such chemical agent can be calcium hydroxide ($Ca(OH)_2$), soluble amines such as diethylenetriamine (DETA), or the like.

An AlP condensed solid was formed and existed as a dispersion of solid acidic AlP particles in water. The suspension was filtered to isolate the acidic AlP particles. The particles were washed with water one or more times, and then filtered again. In an example embodiment, after the initial filtering, the particles were washed with a volume of water approximately six times the volume of the precipitate before being refiltered. Successive washings operate to remove unreacted starting material and any soluble byproducts from production. After being refiltered, the acidic AlP particles were reslurried by the addition of water, and were further treated in accordance with one of the following three different techniques.

In a first technique, the slurry is filtered to isolate the acidic AlP particles and the particles are heated. In an example embodiment, the AlP particles are heated to a temperature of about 110° C. for about 24 hours to drive off the water, and produce acidic AlP particles. Alternatively, the AlP particles are heated to a temperature of about 250° C. for about 12 to 48 hours, and produce acidic AlP particles that are both free of water and any by-products that decompose below 250° C. In addition, heat treatment at either temperature, but especially at the elevated temperature, provides the driving force to complete the conversion of any intermediates that may remain in the complex.

In a second technique, the slurry containing the acidic AlP is neutralized by adding a suitable neutralizing agent thereto. In an example embodiment, the neutralizing agent is ammonium hydroxide ($NH_4OH$) that is added to the slurry in a sufficient amount to increase the pH and to neutralize the AP to a desired pH, typically 5.5 to 7.0. The resulting slurry is filtered and the isolated AP particles are heated. In one example embodiment, the AlP particles are heated to a temperature of about 110° C. for about 24 hours to drive off the water, and produce AlP particles. Alternatively, the AlP particles are heated to a temperature of about 250° C. for about 24 hours to both drive off water and other unwanted chemical constituents, to produce AlP particles and to effect any final conversion or neutralization of surface adsorbed or bulk absorbed reactive species such as phosphate anion or hydrogen phosphate anion. Any reactive amine may be used for this conversion or neutralization step, including but not limited to diethylenetriamine, triethylenetetramine, 2-amino-2-methyl-1-propanol.

In a third technique, the slurry containing the acidic AlP is neutralized by adding a suitable neutralizing agent thereto. In an example embodiment, the neutralizing agent is calcium hydroxide ($Ca(OH)_2$) that is added to the slurry in a sufficient amount to increase the pH and neutralize the acidic AlP. The resulting slurry is filtered and the isolated AlP particles are heated. In one example embodiment, the AlP particles are heated to a temperature of about 110° C. for about 24 hours to drive off the water, and produce AlP particles. Alternatively, the AlP particles are heated to a temperature of about 250° C. for about 24 hours to both drive off water and other unwanted chemical constituents, and produce AlP particles. Other hydroxide compounds of such divalent cations as barium, and magnesium may be used in place of calcium to effect the neutralization or pH adjustment.

As described above in Example 1, the AlP produced according to the methods disclosed in Example 2 comprised AAlP. However, it is to be understood that crystalline AlP and/or combinations of AAlP and crystalline AlP can be produced according to the methods disclosed, e.g., by running the condensation reaction at temperatures for periods of time of less than 3 hours above 90° C. Maintaining the reaction temperature between about 45 and 90° C., and preferably between about 60 and 70° C. will produce AlP that is a combination of crystalline and amorphous forms. Running the reaction at a temperature below about 45° C. will produce primarily AlP in the amorphous form.

Example No. 3

Binary Condensation Formation of the AlP (Acid-to-Base Route)

It has been discovered that changing the order of addition changes the nature of the catalysis of the condensation reaction, i.e., adding the acid to the basic slurry results in slower localized pH change and the reaction is primarily base catalyzed. The AlP particles form slower and are smaller in localized areas in solution. The particles that form tend to have higher surface areas than particles formed by acid catalysis, and are less aggregated and agglomerated. In an example embodiment, the order of addition in Example 2 is reversed, that is, the required amount of phosphoric acid is added slowly to the aluminum hydroxide slurry. The slurry is prepared as described in Example 2. Phosphoric acid is added slowly to the slurry over a period of approximately 30 minutes to one hour, and the resulting mixture is mechanically stirred and heated to about 95° C. for at least 3 hours. The AlP particles are isolated and purified, and dried as described in Example 2.

In addition to the acid-to-base route disclosed immediately above, it has been discovered that such acid-to-base route can be further enhanced by first dissolving a certain amount of the aluminum hydroxide in the phosphoric acid before adding the acid solution to the slurry. In an example embodiment, an amount of aluminum hydroxide, e.g., up to the solubility limit of aluminum hydroxide, is dissolved separately in the phosphoric acid. In an example embodiment, AlP is prepared according to a two-step process. In a first step, a portion of the aluminum hydroxide, typically one third of the stoichiometric amount, is first dissolved in phosphoric acid to form an acidic AlP solution. This acidic AlP solution contains all the phosphoric acid and phosphate needed to satisfy the stoichiometry of the reaction for a product having the desired 1:1 P to Al ratio. In a second step, the acidic AlP solution is then added to a slurry containing the remaining amount of aluminum hydroxide required for stoichiometry. The combination undergoes reaction at ambient temperature to form an AlP condensed solid comprising a dispersion of solid acidic AlP particles in water. Alternatively, the reaction can occur at elevated temperature conditions, e.g., of about 95° C., which is preferred for reaction efficiency and kinetic control of product forms. An advantage of this two-step approach is that part of the aluminum hydroxide required for the reaction is dissolved and pre-reacted before the acid solution is added to the slurry, thereby providing a subsequent heterogeneous reaction that is less viscous and requires less agitation, to thereby ensure more complete condensation.

Like the method disclosed in Example 2 above, such acid-to-base reaction routes are ones that are preferably conducted under constant volume conditions. The suspension was filtered to isolate the acidic AlP particles. The particles were washed with water one or more times, and then filtered again. In an example embodiment, after the initial filtering, the particles were washed with a volume of water approximately six times the volume of the precipitate before being refiltered. In a preferred embodiment, the sequence is to filter and wash, which can be repeated any number of times to achieve the desired degree of purity. The resulting rewashed AlP particles can then be filtered and dried at a temperature of approximately 110° C. for about 24 hours to provide acidic AlP particles.

Alternatively, after rewashing, the AlP particles can be reslurried and then neutralized by adding a suitable neutralizing agent, e.g., such as those described above, thereto. In an example embodiment, a sufficient quantity of ammonium hydroxide ($NH_4OH$) was added to the reslurried AP, and the resulting mixture was filtered to isolate the AlP particles, and the particles are heated. In an example embodiment, the AlP particles are heated to a temperature of about 110° C. for about 24 hours to drive off the water, and produce solid AAlP particles. Additionally, as described above, it is to be understood that the method disclosed herein can also be used to produce crystalline AlP or combinations of AAlP and crystalline AlP, e.g., by running the reaction at temperatures in excess of about 90° C.

Example 4

Binary Condensation Formation of the AlP (Base-to-Acid In-Situ Aggregation)

In an example embodiment, AlP is prepared by adding aluminum hydroxide ($Al(OH)_3$) to phosphoric acid ($H_3PO_4$) to form the desired AlP, e.g., in the manner disclosed above in Examples 1 and 2. However, unlike Examples 1 and 2, the reaction is allowed to occur in an open system, wherein the reaction system is left open so as to allow solvent water to continuously evaporate, thereby causing the concentration of the reaction system to increase and its pH to decrease over time. At periodic intervals during the condensation reaction process, the water level is replenished to the initial volume. The reaction slurry is then diluted with an additional 50 g of water and stirred for 30 minutes to further facilitate dispersion of the AlP particles in the reaction slurry. The slurry is then filtered, washed with a volume of water approximately six times the volume of the precipitate, and filtered again. This filter-wash-filter cycle can be repeated until the desired purity level is achieved. Usually one to three cycles is sufficient to remove unreacted starting material and unwanted reaction by-products.

It has been discovered that by allowing the volume to vary as described, the resulting change in system concentration and pH causes sequential precipitation of AlP "oligomers" in solution onto AlP particles already formed and agglomerated. This sequential precipitation of AlP oligomers onto already-formed and agglomerated AlP particles operates to seal the surface porosity of the pre-existing AlP aggregates and particles, e.g., causing in-situ particle layering, which thereby reduces the surface porosity of such AlP aggregate and reduces such related properties as oil absorption. In an example embodiment, the AlP oligomers are AAlP and the AlP particles already formed are AAlP.

As noted above, allowing water levels to cycle during the condensation causes a change in the pH proportional to the concentration of the $Al(OH)_3$. When the volume decreases, the pH increases due to the higher concentration of the $Al(OH)_3$, and the solubility decreases allowing AlP oligomers to agglomerate. Adding $Ca(OH)_2$ to the condensation medium may also effect a similar change in pH, causing the precipitation of AlP and subsequent coating of pre-existing AlP particles. This process would also incorporate the alkaline earth metal cations as counter-ions for residual acid phosphate groups either adsorbed on the AlP particle surface or bonded as a pendant component.

A condensed solid was formed and existed as a dispersion of solid acidic-coated AAlP particles in water. The suspension was filtered to isolate the acidic coated AlP particles. The particles were washed with water one or more times, and then filtered again. In an example embodiment, after the initial filtering the particles were washed with a volume of water approximately six times the volume of the precipitate before being refiltered. Successive washings remove unreacted starting material and any byproducts from production. After being refiltered, the acidic-coated AlP particles were reslurried by the addition of water, and were further heat treated. In an example embodiment, the slurry is filtered to isolate the acidic coated AlP particles and the particles are heated to a temperature of about 110° C. for about 24 hours to drive off the water, and produce acidic coated AlP particles. Alternatively, the coated AlP particles are heated to a temperature of about 250° C. for about 12 to 48 hours, to produce dry acidic coated AP particles that are both free of water and any by-products that decompose below 250° C. Additionally, as described above, it is to be understood that the method disclosed herein can be used to produce crystalline AlP, or a combination of AAlP and crystalline AlP.

Example 5

Binary Condensation Formation of AlP (Acid-to-Base In-Situ Aggregation)

In an example embodiment, AlP is prepared by adding phosphoric acid ($H_3PO_4$) to aluminum hydroxide ($Al(OH)_3$) to form the desired AlP, e.g., in the manner disclosed above in Example 3. However, unlike Example 3, the reaction is allowed to occur in an open system, wherein the reaction system is left open so as to allow solvent water to continuously evaporate, thereby causing the concentration of the reaction system to increase and its pH to decrease over time. At periodic intervals during the condensation reaction process, the water level is replenished to the initial volume. The reaction slurry is then diluted with an additional 50 g of water and stirred for 30 minutes to further facilitate dispersion of the AlP particles in the reaction slurry. The slurry is then filtered, washed with a volume of water approximately six times the volume of the precipitate, and filtered again. This filter-wash-filter cycle can be repeated until the desired purity level is achieved. Usually one to three cycles is sufficient to remove unreacted starting material and unwanted reaction by-products.

As noted above in Example 4, it has been discovered that by allowing the volume to vary as described during the reaction, the resulting change in system concentration and pH causes sequential precipitation of AlP "oligomers" in solution onto AlP particles already formed and agglomerated. This sequential precipitation of AlP oligomers onto already-formed and agglomerated AlP particles operates to seal the surface porosity of the pre-existing AlP aggregates and particles, e.g., causing in-situ particle layering, which thereby reduces the surface porosity of such AP aggregate and reduces such related properties as oil absorption. In an example embodiment, the AP oligomers are AAlP and the AlP particles already formed are AAlP. Additionally, as described above, it is to be understood that the method disclosed herein can be used to produce crystalline AlP, or combinations of AAlP and crystalline AlP.

Example No. 6

Formation of the Bioactive-AlP Complex (Physical Incorporation)

The AlP made as a binary condensation product, e.g., as set forth in Example Nos. 1 to 5, was constituted as a 34 percent by weight slurry, and was mixed with appropriate concentration silver nitrate solution. The later solution was made so that a 1.0% percent and a 10% percent silver-to-AlP slurry solution was prepared. The combined slurry was mixed for approximately 5 minutes and then atomized in a spray drier under nitrogen, and dried at temperatures ranging from about 180° C. inlet to about 79° C. outlet. The solid powder was collected and analyzed. The resulting powder was a bioactive-AlP complex where the bioactive material was physically incorporated, enmeshed, encapsulated, or intertwined in the AlP polymer.

Alternatively, the AlP made as a binary condensation product, e.g., as set forth in Example Nos. 1 to 5, was constituted as a 34 percent by weight slurry, and was mixed with appropriate concentration silver nitrate solution. After stirring the combined slurry was filtered and washed once with hot water at a temperature of 40 to 60° C. The filtrate was dried at approximately 110° C. for approximately 12 hours, divided into portions, and each heat treated for approximately 24 hours at approximately 250° C. Yields were the same regardless of heat treatment temperature, and the resulting powder was a bioactive-AlP complex where the bioactive material was physically incorporated, enmeshed, encapsulated, or intertwined in the AlP polymer.

Example No. 7

Formation of the Bioactive-AlP Complex (Chemical Bonding)

AlPs were prepared by the binary condensation routes described above in Example Nos. 1 to 5, except that a silver nitrate solution of appropriate concentration was combined at the same time as the phosphoric acid and aluminum hydroxide where brought together. The resulting suspension comprised the bioactive-AlP complex condensate in solution, wherein the bioactive material, in the form of silver ion, was chemically bonded with the AlP polymer, e.g., incorporated into the AlP polymer backbone. The suspension was filtered in the manner described above, to isolate the bioactive-AlP complex particles. The particles were washed and dried at the temperatures described in the above-noted Examples to provide the desired engineered physical properties or characteristics, e.g., porosity.

In these example processes, a chemical reaction results in the formation of amorphous aluminum orthophosphate or of aluminum orthophosphates ($Al_2(HPO_4)_3$ or $Al(H_2PO_4)_3$. The reaction, is carried out through the mixture of the two ingredients (when forming the AlP separately), or through the mixture of the three ingredients (when directly forming the bioactive-AlP complex). The reagents are dosed in a reactor equipped with a stirring device, and allowed to react for a short period of time, e.g., less than about 10 minutes.

Precipitation Methods of Making

The AlP is a phosphate complex prepared by dissolving a suitable salt, such as aluminum hydroxide, magnesium hydroxide, calcium hydroxide, aluminum sulfate and the like in phosphoric acid in molar amounts to achieve complete dissolution of the salt. The phosphate complex is precipitated from the acid solution by neutralizing with an alkaline solution or base such as sodium hydroxide, potassium hydroxide, ammonium hydroxide, sodium aluminate, potassium aluminate and the like. The composition of the resulting precipitated solid depends on the ratio of the metal to the phosphate anion. The properties of the precipitated complex, i.e., AlP, depend on the processing parameters employed during the dissolution of the salt in the acid and on the conditions of the precipitation/neutralization, including choice of neutralizing agent, temperature, order of addition of reactants, rate of addition of reactants, and the degree and duration of agitation.

AlPs are made as a precipitation product by combining selected starting materials including an aluminum source and a phosphorous source under specific conditions of controlled material delivery, temperature, agitation, and pH. The judicious selection of starting materials and process conditions produces AlPs having a material content and chemical structure intentionally created with the purpose of producing the above-noted engineered physical property or characteristic, e.g., porosity, the provides the desired controlled delivery/release of the bioactive constituent.

Aluminum sources useful for forming AlP by-precipitation include aluminum salts, such as aluminum chloride, aluminum nitrate, aluminum sulfate and the like. Aluminum sources useful for forming AlP also include aluminate compounds, such as sodium aluminate and the like, aluminum hydroxide, or aluminum in metallic form. Phosphorous sources useful for forming AlP by precipitation include phosphoric acid, and salts of phosphorus as orthophosphates or as polyphosphates. An alkaline solution is used to control the pH or neutralize the reaction of the main ingredients. In an example embodiment, the alkaline solution can include ammonium hydroxide, sodium hydroxide, sodium carbonate, and combinations thereof. In an example embodiment, sodium hydroxide is used as the alkaline solution. Useful aluminum sources, phosphate sources, and alkaline sources include those disclosed in Published US Patent Applications 2006/0045831 and 2008/0038556, which are each incorporated herein by reference in their entirety.

AlPs can be made through the selective combination of the materials noted above. The following selected methods of preparation are provided below as examples, and it is to be understood that other methods of preparation other than those specifically disclosed may be used. While AlPs produced according to the precipitation route as better disclosed below comprise amorphous AlPs, it is to be understood that the precipitation methods of making AlP as disclosed herein can also be used or adapted to produce crystalline AlP or combinations of amorphous and crystalline AlP depending on the particular desired antimicrobial chemical composition properties.

Example No. 8

Aluminum Sulfate Method of Making AlP

In an example embodiment, AlP having the above-noted engineered properties is prepared by combining aluminum sulfate, phosphoric acid and sodium hydroxide as disclosed in U.S. Pat. No. 7,951,309, which is incorporated herein by reference. The process steps used in this example process generally include: preparing the main reagents, such as a diluted solution of phosphoric acid, a diluted solution of aluminum sulfate, and a diluted solution of sodium hydroxide or ammonium hydroxide; simultaneous and controlled adding of the reagents in a reactor equipped with a sloshing system to keep the homogeneity of the mixture during the process; and controlling, during the addition of the reagents in the reactor, of the temperature and pH (acidity) of the mixture and the reaction time.

The main reagents in this example process can be prepared as follows. A source of phosphorus is fertilizer grade phosphoric acid, from any origin, that has been clarified and discolored. For example, a commercial phosphoric acid containing approximately 54% of $P_2O_5$ may be chemically treated and/or diluted with treated water resulting in a concentration of approximately 20% $P_2O_5$. Another reagent useful for this example process is commercial aluminum sulfate, which may be obtained by reaction between alumina (hydrate aluminum oxide) and concentrated sulfuric acid (98% $H_2SO_4$), that is clarified and stored at an approximate 28% concentration of $Al_2O_3$. For the reaction to have favorable kinetics, the aluminum sulfate is diluted with water treated at approximately 5% of $Al_2O_3$.

Neutralization of the reaction is carried out with a sodium hydroxide solution, which may be commercially purchased in different concentrations. A concentration of approximately 50% of NaOH may be purchased and diluted. For example, in a first phase of the reaction, when the initial reagents are being mixed, the sodium hydroxide may be used in the concentration of approximately 20% of NaOH. In a second phase of the reaction, to fine tune the product acidity, a sodium hydroxide solution with approximately 5% of NaOH may be used. As an alternative neutralizer, ammonium hydroxide or sodium carbonate (soda ash) may be used.

In this example process, a chemical reaction results in the formation of amorphous aluminum orthophosphate or of aluminum orthophosphates ($Al_2(HPO_4)_3$ or $Al(H_2PO_4)_3$. The reaction is carried out through the mixture of the three reagents, i.e., phosphoric acid solution, aluminum sulfate solution, and sodium hydroxide solution. The reagents are dosed in a reactor, typically containing a sloshing system, during about a 30 minute period. During the addition of the reagents in the reactor, the pH of the mixture is controlled within a 4 to 4.5 range and a reaction temperature, between 35° C. and 40° C. The reaction is completed after about 15 minutes of the reagent mixture. In this period, the pH of the mixture may be adjusted to 5, with the addition of more diluted sodium hydroxide. In this example process, the temperature is preferably maintained below approximately 40° C. At the end of the reaction, the suspension formed should contain a P:Al molar ratio of between about 0.8:1 to 1.2:1.

After the formation of the AlP, the suspension containing around 6.0% to 10.0% of solids, with a maximum approximate temperature of about 45° C., and density of about 1.15 to 1.25 g/cm$^3$, is processed for separation. In an example embodiment, the suspension is pumped to a conventional filter press. In the filter press, the liquid phase (sometimes referred to as the "liquor") is separated from the solid phase (sometimes referred to as the "cake"). The wet cake, containing approximately 35% to 45% of solids is kept in the filter for washing cycle. The filtered concentrate, which is basically a concentrated solution of sodium sulfate, is extracted from the filter and stored for future usage. While the use of a filter press has been disclosed as a separating technique, it is to be understood that other types of separating techniques can be used.

In an example embodiment, washing of the wet cake is performed in the filter itself and in multiple process steps. In a first washing ("displacement washing") the largest part of the filtered substance contaminating the cake is removed. The washing step is performed using treated water over the cake flowing at a preselected flow rate. A second washing step, also with treated water, may be carried out to further reduce, if not eliminate, the contaminants. A third washing step using a slightly alkaline solution may be used to neutralize the cake and to keep its pH in the 7.0 range. The cake may be blown with compressed air for a period of time. Preferably, the solids content of the wet product is between about 35% to 45%. While the use of a particular washing technique and sequence has been disclosed, it is to be understood that other types of washing techniques can be used.

The cake dispersion may be processed in such a way that the filter cake, wet and washed, and containing approximately 35% of solids, is extracted from the press filter by a conveyor belt and transferred to a reactor/disperser. The dispersion of the cake is aided by the addition of a dilute solution of sodium tetrapyrophosphate.

After the dispersion step, the product is then dried, when the AAlP "mud," with a percentage of solids of between about 30% to 50%, is pumped to the drying unit. In an example embodiment, water removal from the material can be carried out with drying equipment, such as a "turbo dryer" type through an injection of a hot air stream, at a temperature of less than about 300° C., preferably temperatures of from about 100° C. to 200° C. as noted above to obtain the desired engineered porosity. While the use of a particular drying technique has been disclosed, it is to be understood that other types of drying techniques can be used.

Example No. 9

Sodium Aluminate Method of Making AlP

In another example process, the AlP is prepared by using sodium aluminate as an aluminum source as disclosed in U.S. Pat. No. 7,951,309. In one such embodiment, the AAlP is prepared by a reaction between phosphoric acid and aluminum hydroxide. The process may further comprise a step of neutralizing that can be carried out by using sodium aluminate. In certain embodiments, the process for making an AlP comprises reacting phosphoric acid, aluminum hydroxide and sodium aluminate. In one embodiment, the process for making an amorphous sodium aluminum phosphate comprises reacting aluminum phosphate and sodium aluminate.

In one embodiment, the reaction comprises two steps. In a first step, phosphoric acid reacts with aluminum hydroxide to produce aluminum phosphate at an acidic pH. In one embodiment, AlP is produced as a water soluble aluminum phosphate. In certain embodiments, the pH of water soluble AlP is less than about 3.5. In certain embodiments, the pH is about 3, 2.5, 2, 1.5 or 1. In certain embodiments, AAlP is produced as a fine solid-liquid dispersion at a higher pH. In one embodiment, the pH is about 3, 4, 5 or 6.

In a second step, the acidic aqueous aluminum phosphate solution or dispersion from the first chemical step is reacted with sodium aluminate. In certain embodiments, the sodium aluminate is used as an aqueous solution at a pH greater than about 10. In one embodiment, the pH of the aqueous sodium aluminate solution is about 11, 12 or 13. In one embodiment, the pH of the aqueous sodium aluminate solution is greater than about 12. The AAlP is generated as a solid precipitate. In one embodiment, the solid aluminum-sodium phosphate has a molar ratio of P:Al of about 0.85, and a molar ratio of Na:Al of about 0.50. In one embodiment, the solid AAlP has a molar ratio of P:Al of about 1, and a molar ratio of Na:Al of about 0.76. In certain embodiments, the molecules with other formulation ratios can be obtained by the same procedure.

In one embodiment, the solid hydrated aluminum hydroxide is added to the phosphoric acid in the first chemical step. In another embodiment, the solid hydrated aluminum hydroxide is added to the purified liquid sodium aluminate solution to form a colloidal solution. In another embodiment, the solid hydrated aluminum hydroxide is added directly as solid or solid-liquid suspension in water in the second reaction step. In certain embodiments, the reaction is carried out in a single step.

Sodium aluminates useful for this example process include those that can be obtained by methods known to those skilled in the art. For example, the sodium aluminate can be provided in solution form as a standard chemical product resulting from the first step in the Bayer process in the alumina ($Al_2O_3$) extraction from Bauxite ore, often called "purified sodium pregnant solution". This liquid aqueous sodium aluminate solution is saturated at ambient temperature and stabilized with sodium hydroxide, NaOH. It's typical compositions are: sodium aluminate, 58 to 65% mass (25 to 28% mass of $Al_2O_3$) and sodium hydroxide, 3.5 to 5.5% mass (2.5 to 4% mass of free $Na_2O$). In certain embodiments, it has a molar ratio of Na:Al of from about 1.10 to 2.20 and low impurities (depending on the Bauxite origin: Fe=40 ppm, Heavy metals=20 ppm, and small amount of anions, $Cl^-$ and $SO_4^{2-}$). In certain embodiments, the sodium aluminate water solution has a molar ratio of Na:Al of about 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.0, 2.05, 2.10, 2.15 or 2.2. The solution color, in certain embodiments, is amber. In certain embodiments, the viscosity of the solution is approximately 100 cP. In certain aspects, the sodium aluminate solution is purified by polishing filtration. In certain embodiments, the sodium aluminate solution is regenerated from solid aluminum hydroxide and sodium hydroxide.

The solid hydrated aluminum hydroxide can be obtained by methods known to one of skill in the art. In one embodiment, aluminum hydroxide is an industrial chemical produced by the Bayer process. The solid hydrated aluminum hydroxide can be obtained from the "purified sodium aluminate pregnant solution" by precipitation which is accomplished via cooling the solution. In one embodiment, the sodium aluminate thus produced has a low level of impurities and a variable amount of humidity (cations about 70 ppm, chlorates about 0.85% mass and sulfates about 0.60% mass (these impurities are determined by the purification level of the "Purified Sodium Aluminate pregnant solution) and the total water, hydration and humidity, about 22.0 to 23.5% mass. In one aspect, both raw materials are standard primary industrial products, just first and second step from the bauxite processing, (commodities) produced in huge amounts by the bauxite processors.

In one embodiment, the chemical reaction results in the formation of aluminum sodium phosphate ($Al(OH)_7Na_7(PO_4).1.7H_2O$). After the formation of aluminum sodium phosphate, the suspension containing around 6% to 10% of solids, with a maximum approximate temperature of 45° C., and density in a 1.15 to 1.25 g/cm³ range, is pumped to a conventional filter press.

In a preferred embodiment, AlP prepared by the precipitation process is prepared by using sodium aluminate. It has been discovered that the sodium aluminate process provides for an improved degree of control over the desired characteristics of the AlP that does not otherwise exist in the aluminum sulfate process.

Example No. 10

Formation of the Bioactive-AlP Complex (Physical Incorporation)

The AlP made by the precipitation methods described above in Example Nos. 8 and 9, was constituted as a 34 percent by weight slurry, and was mixed with appropriate concentration silver nitrate solution. The later solution was made so that a 1.0 percent and a 10 percent by weight silver-to-AlP complex was made and a slurry solution was prepared. The combined slurry was mixed for approximately 5 minutes and then atomized in a spray drier under nitrogen, and dried at temperatures ranging from about 180° C. inlet to about 79° C. outlet. The solid powder was collected and analyzed. The resulting powder was a bioactive-AlP complex where the bioactive material was physically incorporated, enmeshed, encapsulated, or intertwined in the AlP polymer.

Alternatively, the AlP made by the precipitation processes disclosed above was constituted as a 34 percent by weight slurry, and was mixed with appropriate concentration silver nitrate solution. After stirring the combined slurry was filtered and washed once with hot water at a temperature of 40 to 60° C. The filtrate was dried at approximately 110° C. for approximately 12 hours, divided into portions, and each heat treated for approximately 24 hours at approximately 250° C. Yields were the same regardless of heat treatment temperature, and the resulting powder was a bioactive-AlP complex where the bioactive material was physically incorporated, enmeshed, encapsulated, or intertwined in the AlP polymer.

Example No. 11

Formation of the Bioactive-ALP Complex (Chemical Bonding)

An AlP was prepared similar to the precipitation process described above in Example Nos. 8 and 9, except that a silver nitrate solution of appropriate concentration was combined with the acidic aluminum phosphate solution (P:Al ratio of 3:1) and then neutralized with an appropriate amount of sodium aluminate. The resulting dispersion comprised the bioactive-AlP complex, wherein the bioactive material, in the form of silver ion, was chemically bonded with, e.g., incorporated into the polymer backbone of, the AlP polymer. The dispersion was filtered to isolate the bioactive-AALP complex particles. The particles were washed and dried at the temperatures described above to provide the desired engineered porosity.

Sol Gel Method of Making

AlP prepared by a sol-gel process involves the creation of inorganic molecular networks from molecular or ionic precursors through the formation of a colloidal suspension (sol) and the gelation of such sol to form a solid network in a continuous liquid phase (gel). The precursors for synthesizing these colloids typically comprise a metal or metalloid element surrounded by various reactive groups. Stated another way, in the sol gel process, simple molecular or ionic precursors are converted into nano-sized particles to form a colloidal suspension (sol). The colloidal nano-particles are then linked with one another in a three-dimensional liquid filled solid network (gel). This transformation to a gel can be initiated in a number of ways, but the most convenient approach is to change the pH of the reaction solution.

The method used to remove the liquid from the solid will affect the sol gel's properties. For example, supercritical drying will maintain the three-dimensional structure in the dried solid, whereas slow drying in a fluid evaporation process collapses the network structure creating a high density material.

Advantages to preparing the AlP via a sol gel synthesis process include process versatility and simplicity resulting in the possibility to obtain highly pure and/or tailored materials, uniform particle size distribution, substantially spherical-shaped aggregate particles, nano-sized particles, and custom engineered compositions. While AlP as disclosed herein comprises substantially spherical aggregate particles, it is understood that some small amount of nonspherical particles may unintentionally be produced and may be present in the resulting antimicrobial chemical compositions.

As used herein, the term "gel" is understood to be a three-dimensional cage structure formed of linked large molecular mass polymers or aggregates in which liquid is trapped. The network of the structure typically consists of weak and/or reversible bonds between the core particles. The term "sol" as used herein is understood to be a colloidal dispersion of solids in a liquid. The solids comprise aluminum phosphate having nanometer scale average particle sizes. The gel comprises an aluminum phosphate sol as a dispersed phase in a semi-rigid mass enclosing all of the liquid. Post treatment of product produced by the sol gel process by filtration, washing, drying, and combinations thereof leads to aggregation of the colloidal solids in a controlled fashion to form a larger solid complex.

Generally, the sol gel process includes the following process steps: (1) nucleation or polymerization or condensation of the molecular precursors to form primary particles, e.g., nanometer in scale, to form the sol (colloidal dispersion or suspension); (2) growth of the particles or gelation; (3) linkage of the particles to form chains and the extension of such chains throughout the liquid medium to form a thickened gel; and (4) treating the sol gel material to remove the liquid to give a desired solid end-product.

In an example embodiment, the precursor solution is prepared by combining a suitable aluminum source, with a phosphorous source. Suitable aluminum sources can be selected from the group of aluminum salts such as aluminum chloride, aluminum nitrate, aluminum sulfate and the like. A preferred aluminum source is aluminum nitrate. Phosphorous sources useful for forming AAlP by sol gel process include phosphoric acid, and salts of phosphorus as orthophosphates or as polyphosphates. A source of phosphorus is fertilizer grade phosphoric acid, from any origin, that has been clarified and discolored.

The primary ingredients of the precursor solution are combined together in an aqueous environment with a gelling agent to produce a colloidal dispersion of solid aluminum phosphate particles in solution. In an example embodiment, the precursor solution is formed by combining aluminum nitrate with phosphoric acid (85% by weight) in the presence of water. Water can be present in one or more of the aluminum nitrate, the phosphoric acid, or as added water independent of either ingredient.

After the precursor ingredients are combined, the resulting system is stirred and a suitable alkaline ingredient is added to the stirred solution. Alkaline ingredients useful for this purpose include those conventionally used to change the pH of the system, e.g., increase the pH of the acidic system, and in an example embodiment is ammonium hydroxide. The presence of the ammonium hydroxide increases the pH and drives the process of nucleation and condensation forming a colloidal dispersion or sol. Depending on the concentration of nucleating agent, this step can be intermediate or final. Further addition of nucleating agent causes the primary aluminum phosphate particles to link together forming a gel, e.g., results in gelation, and further results in the colloidal particles being linked into the gel structure to form a sol gel.

In an example embodiment, it may be desired to control the sol gel process to isolate the colloidal dispersion before gelation. This can be done by controlling the reaction conditions so that only colloidal dispersion occurs (i.e., formation of a sol) and not full gelation. Controlling the process in this manner may provide certain manufacturing advantages and/or provide certain advantages relating to handling of the end-product. The colloidal dispersion from this process can be filtered to recover the solids, and then thermally treated and/or washed as described below.

In an example embodiment, the phosphoric acid, aluminum nitrate, and/or ammonium hydroxide can be heated prior to being combined with one another, or can be heated after combination, e.g., during stirring. Additionally, the amount of water present and/or the rate of addition of the ammonium hydroxide, can be adjusted to produce a desired reaction product having a desired yield of AAlP.

In an example embodiment that amount of ammonium hydroxide, $NH_4OH$, that is added to the acid solution is sufficient to neutralize the acid system to initiate formation of colloidal aluminum phosphate particles, and for gelation exceeds the stoichiometric amount to form ammonium nitrate, $NH_4NO_3$. The range can be from the stoichiometric amount of $NH_4OH$ needed to form the $NH_4NO_3$ (1.0 stoichiometry) to about 3.0 stoichiometry, preferably between about 1.1 and 2.0, and more preferably between about 1.2 and 1.5.

The order of addition (i.e., base solution to acid precursor solution or vice versa) has been found to control the rate and extent of gelation. When base is added to stirred precursor solution in stoichiometric concentration ranges stated above (1.0 to 3.0) virtually instantaneous gelation occurs. It has been discovered that reversing the order of addition, i.e., adding the precursor solution to the base solution, provides control over the extent of growth from colloidal dispersion to full gelation. As discussed below, it has also been discovered that particle morphology can be controlled by the method of addition.

It has been found that concentrations of ammonia in excess of the 1.1 stoichiometric ratio are useful to minimize unreacted aluminum in the resulting complex. For the end-use application as an inhibitive pigment, it is desirable that the phosphate release rate from the complex when contacted with water be in the 200 to 400 ppm range. Testing has determined that phosphate anion elution is in the target range when the ammonia level in the reaction is around 1.2 to 3 stoichiometric ratio and after the solid has been thoroughly washed and/or thermally treated to remove the soluble by-products as described below.

In an example process, the sol gel is next subjected to post gelation treatment which may comprise heating, washing, and/or sizing. In an example embodiment, the sol gel powder formed is isolated by collapsing the dispersion or gel by driving off the liquid constituent. Various types of gels can be formed from the sol gel such as; xerogels that are solids formed by unhindered drying of the sol gel so as to yield high porosity and surface area (150-1,000 $m^2/g$) in solid form, aerogels that are solids formed by supercritical drying (e.g., freeze drying), hydrogels that are water insoluble colloidal polymer particles dispersed in water, and organogels that are amorphous, non-glassy solids comprising a liquid organic phase trapped in the solid matrix.

The sol gel consists of solid $AlPO_4$ connected through various pH dependent (amino, water, phosphate) linkages to form a solid dispersed phase as a mass enveloping all the liquid, the latter consisting of water and dissolved salts. Heating the gel, to a temperature above about 100° C., evaporates the water and any ammonia and collapses the mass to a solid consisting of aluminum phosphate, $AlPO_4$, and ammonium nitrate, $NH_4NO_3$. Heating the gel or the collapsed gel solid, to a temperature above about 215° C., thermally decomposes the ammonium nitrate, $NH_4NO_3$, thereby eliminating it from the powder product. Heating to temperatures above about 215° C. leads to a decrease in pH, indicating that residual amino groups remaining after thermal decomposition of the ammonium nitrate, $NH_4NO_3$, most likely as substituent's on the PO group, are also thermally decomposed and replaced by hydrogen atoms thereby making the complex acidic. The solid product resulting from this treatment has been shown by analysis to be pure AAlP having a phosphate release rate of around 240 ppm and surface area greater than 125 $m^2$/gram.

Accordingly, the post gelation heat treatment can comprise a single step of heating the sol gel to a relatively high temperature above about 250° C. for a period of time sufficient to achieve water evaporation, collapsing of the mass, and thermally decomposing the ammonium nitrate, $NH_4NO_3$. In an example embodiment, this can be done at about 250° C. for approximately 12 to 72 hours. The resulting product from this heat treatment is substantially aluminum phosphate, i.e., there is very little if any ammonium phosphate or ammonium nitrate.

Alternatively, the post gelation heat treatment can comprise a single step of heating the sol gel at a lower temperature of about above about 100 to 150° C. for a period of time sufficient to achieve water evaporation. In an example embodiment, this can be done at about 110° C. for approximately 1 to 24 hours. The resulting product from this heating or drying treatment is AAlP and ammonium phosphate and ammonium nitrate.

This drying step can be followed by a heat treatment step at a temperature of between about 215 to 300° C. In a preferred embodiment, the drying step is at about 110° C. for about 24 hours, and the heat treatment is about 250° C. for up to 1 to 3 days (16 to 72 hours). The resulting AAlP has a moisture content of from about 5 to 20 percent by weight and the desired engineered porosity. The pH of the heat treated material can be adjusted by re-dispersing the complex and adjusting the pH with ammonium hydroxide solution. The resulting complex is then dried at 100 to 110° C. to remove water and ammonia.

If desired, before drying or heat treatment, the sol gel material can be filtered to separate the solid particles from solution, and the separated solid, e.g., in the form of a cake, can be subjected to one or more wash cycles. The wash cycles use water and operate to rid the solid aluminum phosphate particles of any unwanted solubles, e.g., ammonium compounds such as ammonium nitrate, and ammonium phosphate that have been formed as a reaction by-product. The washed sample can then be dried and/or heat treated in the manner disclosed above to further evaporate water and/or thermally decompose any residual ammonium nitrate and ammonium phosphate in the washed aluminum phosphate, and densify the aluminum phosphate particles.

If desired, the sol material can be dried at about 100° C. to evaporate water and collapse the mass, and the collapsed powder can be washed with water to remove ammonium nitrate, $NH_4NO_3$, to thereby recover instead of thermally decompose the by-product. The washed and dried mass can be heat treated above about 215° C. to thermally decompose any residual ammonium nitrate, $NH_4NO_3$, thereby providing substantially pure AAlP.

The basic chemistry of the sol gel process for forming only the AAlP is presented below as follows:

1. Precursor solution—Combination of all ingredients $Al(NO_3)_3 \cdot 9H_2O + H_3PO_4 + H_2O$ 2. Gelling Agent $3NH_4OH + H_2O$ 3. Sol-gel reaction $AlPO_4 + (NH_4)_3PO_4 + H_2O \rightarrow AlPO_4 + NH_4OH$ Reaction to form AAlP sol gel: as $NH_4OH$ (28% $NH_3$ in water) is added, it neutralizes the acid system and drives formation of insoluble $AlPO_4$, that takes $Al^{+3}$ out of the reaction and allows more $NH_4^{+1}$ to combine with $NO_3^{-1}$ to form soluble $NH_4NO_3$. Depending on the concentration and rate of addition of the $NH_4OH$ colloidal particles of $AlPO_4$ will form. Adding more $NH_3$ to the reaction allows the $AlPO_4$ colloidal particles to aggregate and to eventually form bonds between the particles to form the gel structure.

The amount of $NH_3$ added must exceed the stoichiometric amount required to form $NH_4NO_3$ in order to have sufficient $NH_3$ to control pH and facilitate gel bridging. Depending on the amount of $NH_3$ added, the rate of addition, and the concentration, the gel will consist of a mass of $AlPO_4$ solid particles linked forming a cage, three-dimensional structure encapsulating ammonium nitrate, $NH_4NO_3$, dissolved in water. Ammonium phosphate may also be present as an intermediate, and extending reaction conditions (i.e., by further heating) will lead to full reaction with the aluminum in the system to condense to aluminum phosphate.

4. Filtration and washing—Optional to supplement or replace thermal purification to remove soluble ammonium salts.
5. Dehydration and drying—Drying at above at least 100° C. to evaporate water and collapse the sol gel structure to form a densified solid.

$AlPO_4 + NH_4NO_3$

6. Thermal purification—Thermal treatment at 215 to 250° C. to thermally decompose ammonium nitrate.

$AlPO_4$ (amorphous aluminum phosphate)

If desired, the order of ingredient addition can be changed from that disclosed above. For example, the acid solution may be added to a solution of the ammonium hydroxide in order to control the viscosity of the reaction system and/or impact the surface area of the colloidal solids. Such flexibility in the order of ingredient addition may be advantageous, e.g., for the scale-up of manufacturing where it may be desirable to avoid gelation in favor of the formation of a suspension of colloidal primary particles. The resulting composition after washing, drying and/or thermal treatment is essentially chemically the same regardless of the order of addition. However product morphology is affected by these processing parameters. Adding acid to base results in higher surface area and greater porosity. The sol gel process disclosed herein produces an aluminum phosphate composition consisting essentially of AAlP.

Base-to-acid sequencing causes rapid pH change and the rapid formation of sol particles followed by rapid gelation to form interlinked particles in the gel matrix. This reduces molecular mobility and prevents any further particle growth or morphological change. When acid is added to base, the pH change is slower and localized colloidal aluminum phosphate particles form. No gelation occurs so the system mobility allows for continued competing side reactions (increased solubilization of ammonium nitrate and ammonium phosphate) allowing intermediate species to survive. When dehydration and thermal decomposition occur, small particles of aluminum phosphate exist in the presence of departing water and decomposition products (of ammonium nitrate), leading to more porosity in small aggregated aluminum phosphate particles.

The basic chemistry of the sol gel process for forming only the bioactive-AAlP complex (which involves adding the bioactive material, e.g., in the form of silver nitrate, to the aluminum nitrate and aqueous phosphoric acid) is presented below as follows:

1. Precursor solution—Combination of all ingredients $Al(NO_3)_3 \cdot 9H_2O + H_3PO_4 + H_2O + AgNO_3$ 2. Gelling Agent $3NH_4OH + H_2O$ 3. Sol-gel reaction

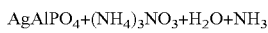

4. Filtration and washing—Optional to supplement or replace thermal purification to remove soluble ammonium salts.
5. Dehydration and drying—Drying at above at least 100° C. to evaporate water and collapse the sol gel structure to form a densified solid.

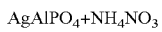

6. Thermal purification—Thermal treatment at 215 to 250° C. to thermally decompose ammonium nitrate.

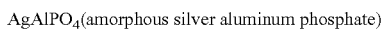

Example No. 12

Formation of the Bioactive-AlP Complex (Physical Incorporation)

The AAlP made by the sol gel process as described above, was constituted as a 34 percent by weight slurry, and was mixed with appropriate concentration silver nitrate solution. The later solution was made so that a 1.0 percent and a 10 percent silver-to-AgAlP complex were prepared. The combined slurry was mixed for approximately 5 minutes and then atomized in a spray drier under nitrogen, and dried at temperatures ranging from about 180° C. inlet to about 79° C. outlet. The solid powder was collected and analyzed. The resulting powder was a bioactive-AlP complex where the bioactive material was physically incorporated, enmeshed, encapsulated, or intertwined in the AlP polymer.

Alternatively, the AAlP made by the sol gel process was constituted as a 34 percent by weight slurry, and was mixed with appropriate concentration silver nitrate solution. After stirring the combined slurry was filtered and washed once with hot water at a temperature of 40 to 60° C. The filtrate was dried at approximately 110° C. for approximately 12 hours, divided into portions, and each heat treated for approximately 24 hours at approximately 250° C. Yields were the same regardless of heat treatment temperature, and the resulting powder was a bioactive-AlP complex where the bioactive material was physically incorporated, enmeshed, encapsulated, or intertwined in the AlP polymer.

Example No. 13

Formation of the Bioactive-AAlP Complex (Chemical Bonding)

An AAlP was prepared similar to the sol gel process described above, except that a silver nitrate solution of appropriate concentration was combined at the same time as the aluminum nitrate and aqueous phosphoric acid. The resulting gel comprised the bioactive-AlP complex, wherein the bioactive material, in the form of silver ion, was chemically bonded with the AlP polymer. The dispersion was filtered, washed, and dried at the temperatures described above to provide the desired engineered porosity.

AlPs/bioactive-AlP complexes formed by the above-noted methods have a P:Al ratio of from about 0.5:1 to 1.5:1. It is desired that the AlPs/bioactive-AlP complexes have a P:Al ratio in this range because this provides a suitable range of particle morphology and properties that are compatible with desired formulation chemistries.

If desired, the bioactive-AlP complex as described herein can be initially made in the form of a concentrate, wherein an amount of the bioactive material is initially combined with a first amount of the AlP (in the case where the bioactive material is physically incorporated with the AlP polymer) or a first amount of the precursor materials used to form the AlP (in the case where the bioactive material is chemically bonded with the AlP polymer). This initially stage results in the formation of a bioactive-AlP complex condensate, i.e., having a high concentration of the bioactive material present. This complex condensate can then be used as feedstock to formulate a number of different formulations to meet different end-use applications. In an example embodiment, the complex condensate may be combined with further AlP to provide a bioactive-AlP complex having a relatively lower bioactive material content that is well suited for a certain end-use application. The ability to make such a complex condensation thereby adds a desired degree of flexibility to the process of obtaining different antimicrobial formulations for meeting different antimicrobial end-use applications.

AlP and bioactive-AlP complexes made in the manner described herein are provided in solid form as a white powder having a desired particle size or size distribution. The particle size will depend on such factors such as the binding polymer, and the particular end-use application. In an example embodiment, the AlP may have a particle size distribution of D50 from about 0.5 to 8 microns. In an example embodiment, it is desired that the AlP have a P:Al ratio of from about 0.9 to 1, and have a particle size distribution of D50 of about 1 micron and D90 less than about 4 microns. For use in an antimicrobial chemical composition it is desired that the AlP have a particle size of less than about 20 microns, and preferably in the range of from about 0.5 to 10 microns, and more preferably in the range of from about 1.0 to 8.0 microns. Particle sizes of less than about 0.5 microns may interfere with the processing of certain chemical formulations and adversely affect film properties by increasing binder resin absorption.

AlP and bioactive-AlP complexes prepared in the manner described above may not be subjected to high-temperature drying or other thermal treatment for the purpose of retaining an amorphous structure and avoiding conversion to a crystalline structure. It has been discovered that AlPs formed in this manner retain the desired amorphous structure, even after low temperature drying. AlPs formed as disclosed herein have a structure comprising an engineered porosity that enables it to serve as a carrier for the bioactive material to provide the desired controlled delivery/release of the bioactive constituent for use in an antimicrobial chemical composition.

AAlPs as produced herein display a markedly increased water adsorption potential or degree of rehydration, when compared to crystalline AlP, that permits such AAlPs, once dehydrated by drying, to be rehydrated to contain up to about 25 percent by weight water. This feature is especially useful when the AlP is used in end-use applications calling for some degree of protection against corrosion, and wherein the AlP is present in a nonwater-borne binding polymer. In such application, the AlP acts, in addition to being a carrier for the bioactive material and being an corrosion inhibiting pigment, as a moisture scavenger to both slow water intrusion into the cured film and restrict water diffusion through the cured film.

Additionally, the rehydration feature of AlPs disclosed herein can be beneficial when placed in low humidity end-use applications. In such applications, AlPs can be used having a high or saturated moisture content that can operate to drive the bioactive constituent, e.g., have a built-in transport mechanism, to a surface of the cured antimicrobial chemical composition or composite to promote the presence of such bioactive constituent at the surface in the absence of surrounding moisture. Engineered in this manner, antimicrobial chemical compositions comprising such AlP can function to provide a desired level of bioactive constituent at the surface in low humidity/moisture applications.

Antimicrobial chemical compositions described herein are prepared by combining a selected binding polymer with the AlP and the bioactive material in the manner and in the amounts described above. The resulting bioactive-AlP complex can be provided for composition formulation in the form of a dried powder or can be provided in the form of a slurry or liquid suspension depending on the formulation conditions or preferences.

Antimicrobial chemical compositions described herein, comprising the bioactive-AlP complex, comprise from about 5 to 1000 ppm, preferably 10 to 900 ppm, and 15 to 800 ppm of the bioactive material based on the total weight of the chemical composition. Such antimicrobial chemical compositions may comprise other materials, agents, and/or additives (in addition to the bioactive-AlP complex and the binding polymer), such as pigments, fillers, rheological agents, flow stabilizers, light-control stabilizers, and the like. For example, antimicrobial chemical compositions comprising a silver bioactive material may comprise an additive designed to inhibit the photo reduction of the silver, to thereby preserve the active state of the silver, contained within the composition, dried film and/or composite formed therefrom, to help ensure its effective service life.

Antimicrobial chemical composition disclosed herein may be provided in the form of a coating composition for applying to a desired substrate surface to provide a desired level of antimicrobial resistance. Such antimicrobial coating compositions can be formulated for use as a primer, a mid coat, or a top coat. Additionally such antimicrobial coating compositions may be used with or without a primer, as a mid or a top coat. Further, antimicrobial chemical compositions as disclosed herein may be formulated as a clear coating for placement over an existing substrate surface or underlying coating that may or may not be colored, thereby facilitating use of such clear coating over a variety of substrates or underlying coating surface to provide antimicrobial resistance without the need for special pigmenting to match existing substrate colors or the like.

Bioactive-AlP complexes as described herein provide bioactive components in a manner that ensures surface antimicrobial efficacy while permitting ease of formulation to meet a variety of end-use applications. The bioactive-AlP complex provides for uniform distribution of the bioactive ingredient, e.g., silver ion, throughout the chemical composition, dried film, composite, or formulated article. The bioactive-AlP complex provides the formulated bulk matrix with properties engineered to accommodate moisture induced transport: absorption, adsorption, desorption, diffusion of water and dissolved species in bulk. The bioactive-AlP complex is specifically engineered to release a bioactive constituent, e.g., silver ion, based on the concentration of the bioactive material incorporated and by the hydrophilicity and morphology of the complex (surface area and porosity). The bioactive-AlP complex as described herein can be introduced into formulated products such as pigments, or as an additive through bonding the phosphate functionality to certain functional groups of the binder matrix of the bulk composite or film. Additionally, the bioactive-AlP complexes in thermally stable form can be incorporated into powder coating formulations to render such surfaces antimicrobial.

In one example embodiment, antimicrobial chemical compositions as described herein can be formulated into a film in which the bulk of the article serves as a reservoir or depot for the bioactive material or its constituent, e.g., silver ion. Such formulation can be engineered to optimize the following aspects of the antimicrobial mechanism: water diffusion into the film, water absorption and adsorption into the bioactive-AlP complex, salt dissolution within the complex, ion transport out of the complex, and bioactive material or its constituent transport through the matrix to the surface to be protected.

Alternatively, the antimicrobial chemical compositions as described herein can be formulated into an enriched thin film (e.g., having a film thickness of less than about 25μ, and preferably less than about 10μ) engineered for physical durability balanced with water diffusion/bioactive material or its constituent transport properties to impart antimicrobial properties to a surface without incorporating the antimicrobial into the bulk of the article, e.g., where such incorporation may not be practical from a cost standpoint, or where the operative control mechanism may not be possible, e.g., a water impermeable plastic.

As described above, the combined AlP and bioactive material is provided in the form of a bioactive-AlP complex, where the bioactive material is either chemically bonded with, e.g., provided in the backbone of the AlP polymer, or is physically incorporated, enmeshed, encapsulated, or intertwined with the AlP polymer, depending on the particular method used to make the complex. Additionally, the bioactive material or its constituent may be present in the AlP polymer both chemically and physically. For example, when the bioactive-AlP complex is formed by combining the desired bioactive material at the time of forming the AlP, thereby facilitating chemical bonding between the bioactive material or its constituent with the AlP, a stoichiometric excess of the additional bioactive material may result in it being physically incorporated into the AlP molecule, in which case the resulting bioactive-AlP complex would include the bioactive material or its constituent present in both chemically-bonded and physically-incorporated form.

As demonstrated above, embodiments of the invention provide a novel antimicrobial chemical compositions, novel bioactive-AlP complexes, and novel methods for making the same. While each has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein.

For example, if desired, antimicrobial chemical compositions can be prepared to additionally include one or more bioactive materials separately or in combination other than those specifically described that are known to have bioactive value. Any such additional bioactive material may or may not be incorporated with the bioactive-AlP complex, e.g., can exist as a separate dispersion with the binding polymer, and can operate to increase or complement or provide a synergistic antimicrobial effect of the chemical composition.

Additionally, while antimicrobial chemical compositions as presented in the examples provided herein have been described as comprising AlP in amorphous form, it is to be understood that antimicrobial chemical compositions as described herein can additionally comprise AlP in its known crystalline forms, and can comprise AlP in a combination of amorphous and crystalline forms.

In other embodiments, the compositions or methods do not include, or are substantially free of, any compounds or steps not enumerated herein. Variations and modifications from the described embodiments exist. The method of making the chemical compositions and/or AlP is described as comprising a number of acts or steps. These steps or acts may be practiced in any sequence or order unless otherwise indicated. Finally, any number disclosed herein should be construed to mean approximate, regardless of whether the word "about" or "approximately" is used in describing the number. The appended claims intend to cover all those modifications and variations as falling within the scope of the invention.

What is claimed:

1. An antimicrobial chemical composition comprising;
a complex comprising a bioactive constituent chemically bonded with and incorporated into a polymer backbone of an amorphous aluminum hydroxyl phosphate, wherein the complex is prepared by combining an aluminum source with a phosphate source in the presence of the bioactive constituent all in an aqueous system, wherein the bioactive constituent comprises silver ions, and wherein the complex has an engineered porosity to provide a controlled release of the silver ion therefrom at a rate upon contact of the complex with moisture, wherein the complex has a porosity characterized by a BET surface area from about 2 to 10 $m^2/g$, a total intrusion volume from about 0.5 to 0.9 mL/g, and an average pore volume from about 0.4 to 0.6 µm;
a binder polymer forming a bulk matrix of the composition, wherein the complex is uniformly dispersed throughout the bulk matrix, wherein the bulk matrix enables the bioactive constituent that is released from the complex to diffuse through the bulk matrix at a rate of diffusion, and wherein the controlled release of the silver ions from the complex is from 10 to 900 ppm when the composition is in the form of a dried film or composite;
wherein the rate of release of the silver ions from the complex is the same or different from the rate of diffusion of the silver ions through the bulk matrix.

2. The chemical composition as recited in claim 1 wherein the complex further comprises one or more metal ions selected from the group consisting of calcium, copper, zinc, and combinations thereof.

3. The chemical composition as recited in claim 1 wherein the aluminum source is aluminum hydroxide and the phosphate source is phosphoric acid.

4. The chemical composition as recited in claim 1 wherein the complex further comprises crystalline aluminum phosphate.

5. The chemical composition as recited in claim 1 wherein the complex consists of the amorphous aluminum hydroxyl phosphate, silver ions, and zinc ions.

6. The chemical composition as recited in claim 1 wherein the rate of release of the bioactive constituent is different from the rate of diffusion of the bioactive constituent.

7. The chemical composition as recited in claim 6 wherein the rate of release of the bioactive constituent is greater than the rate of diffusion of the bioactive constituent.

8. The chemical composition as recited in claim 6 wherein the rate of release of the bioactive constituent is less than the rate of diffusion of the bioactive constituent.

9. The chemical composition as recited in claim 1 wherein the controlled release of the bioactive constituent from the complex is from 15 to 800 ppm.

10. An antimicrobial chemical composition comprising:
a binding polymer;
a bioactive-aluminum phosphate complex uniformly dispersed throughout the binding polymer, the complex comprising amorphous aluminum hydroxyl phosphate and silver ions chemically bonded to and incorporated into a polymer backbone of and dispersed throughout the amorphous aluminum hydroxyl phosphate, wherein the complex is formed by combining aluminum hydroxide with a phosphoric acid in the presence of the silver ions all in an aqueous system;
wherein the aluminum phosphate complex has an engineered porosity with an average pore volume of 0.4 to 0.6 µm that, when the composition is cured, provides a controlled release of the silver ions from 10 to 1,000 ppm when the complex is exposed to moisture.

11. The chemical composition as recited in claim 10 wherein the aluminum phosphate in the complex consists of amorphous aluminum hydroxyl phosphate.

12. The chemical composition as recited in claim 10 wherein the complex comprises crystalline aluminum phosphate.

13. The chemical composition as recited in claim 10 wherein the controlled release of the silver ions from the complex is in the range of from about 15 to 800 ppm.

14. The chemical composition as recited in claim 10 providing a leaching rate of silver ion when in the form of a dried film or composite at a surface of the film or composite at least about 30 µg/$m^2$.

15. The chemical composition as recited in claim 10 wherein the amount of the silver ions present in the complex is in the range of from 1 to 10 percent of the total weight of the complex.

16. The chemical composition as recited in claim 10 wherein the ratio of phosphate to aluminum is in the range of from about 0.5:1 to 1.5:1.

17. The chemical composition as recited in claim 10 wherein the complex has a total intrusion volume of from about 0.5 to 0.9 mL/g.

18. The chemical composition as recited in claim 10 wherein the complex further includes one or more metal ions selected from the group consisting of, calcium, copper, zinc and combinations thereof.

19. The chemical composition as recited in claim 18 wherein the complex includes zinc ions.

20. The chemical composition as recited in claim 10 wherein the aluminum phosphate complex has a BET surface area of from 2 to 10 $m^2/g$, and a total intrusion volume of from 0.5 to 0.9 mL/g.

21. The chemical composition as recited in claim 10 wherein the complex consists of the amorphous aluminum hydroxyl phosphate and silver ions.

22. The chemical composition as recited in claim 10 wherein the complex consists of the amorphous aluminum hydroxyl phosphate, silver ions and zinc ions.

23. The chemical composition as recited in claim 10 wherein silver ions are released from the complex at a rate of release, and wherein the silver ions released from the complex pass through the binder polymer at a rate of diffusion that is different from the complex rate of release.

24. The chemical composition as recited in claim 23 wherein the rate of release is greater than the rate of diffusion.

25. The chemical composition as recited in claim 23 wherein the rate of release is less than the rate of diffusion.

26. The chemical composition as recited in claim 10 wherein the amorphous aluminum hydroxyl phosphate in the complex has a surface area of less than about 10 $m^2/g$.

27. The chemical composition as recited in claim 10 comprising in the range of from about 0.01 to 1 weight percent of the silver ions based on the total weight of the chemical composition.

28. The chemical composition as recited in claim 10 comprising in the range of from about 0.05 to 5 weight percent of the complex based on the total weight of the chemical composition.

29. The chemical composition as recited in claim 10 comprising in the range of from about 0.1 to 2 weight percent of the complex based on the total weight of the chemical composition.

30. The chemical composition as recited in claim 10 wherein the binding polymer is selected from the group consisting of polyurethanes, polyesters, solvent-based epoxies, solventless epoxies, water-borne epoxies, epoxy copolymers, acrylics, acrylic copolymers, silicones, silicone copolymers, polysiloxanes, polysiloxane copolymers, alkyds and combinations thereof.

31. The chemical composition as recited in claim 10 wherein the bioactive-aluminum phosphate complex has a water adsorption potential of up to about 25 percent by weight water.

32. The chemical composition as recited in claim 10 wherein the bioactive-aluminum phosphate complex has a controlled delivery of phosphate anion of less than about 1,500 ppm upon exposure to moisture.

33. The chemical composition as recited in claim 32 wherein the controlled delivery of phosphate anion is between about 100 to 500 ppm.

34. An antimicrobial chemical composition comprising;
a complex comprising a bioactive constituent chemically bonded with and incorporated into a polymer backbone of an aluminum phosphate, wherein the aluminum phosphate consists of amorphous aluminum hydroxyl phosphate and the bioactive constituent comprises silver ions and one or more metal ions selected from the group consisting of calcium, copper, and zinc, wherein the complex has an engineered porosity to provide a controlled release of the silver ions therefrom, wherein the porosity is characterized by a BET surface area from about 2 to 10 $m^2/g$, a total intrusion volume from about 0.5 to 0.9 mL/g, and an average pore volume from about 0.4 to 0.6 µm;
a binder polymer forming a bulk matrix of the composition, wherein the complex is uniformly dispersed throughout the bulk matrix, wherein the bulk matrix enables the bioactive constituent released from the complex to diffuse through the bulk matrix at a rate of diffusion, wherein the rate of release of the silver ions from the complex is the same or different from the rate of diffusion of the silver ions through the bulk matrix, and wherein the controlled release of the silver ions from the complex is from 15 to 800 ppm when the composition is in the form of a dried film or composite to provide a leaching rate at a surface of the dried film or composite of at least about 30 µg/$m^2$.

* * * * *